United States Patent
Tillyer et al.

(10) Patent No.: US 6,569,461 B1
(45) Date of Patent: May 27, 2003

(54) DIHYDROXY OPEN-ACID AND SALTS OF HMG-COA REDUCTASE INHIBITORS

(75) Inventors: Richard D. Tillyer, Cranford, NJ (US); Paul J. Reider, Westfield, NJ (US); Edward J. J. Grabowski, Westfield, NJ (US); Feng Xu, Staten Island, NY (US); Jose M. Vega, Trappe, PA (US); Mandana Asgharnejad, Ambler, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/558,800

(22) Filed: Apr. 26, 2000

Related U.S. Application Data

(63) Continuation-in-part of application No. 09/516,259, filed on Feb. 29, 2000, which is a continuation-in-part of application No. 09/264,744, filed on Mar. 9, 1999.
(60) Provisional application No. 60/123,227, filed on Mar. 8, 1999.

(51) Int. Cl.[7] .............................. A61K 9/00; A61K 9/20; A61K 9/32; A61K 9/16; A61K 9/50
(52) U.S. Cl. ........................ 424/497; 424/400; 424/464; 424/465; 424/482; 424/490
(58) Field of Search .................................... 424/400, 490, 424/497, 482, 464, 465

(56) References Cited

U.S. PATENT DOCUMENTS

| | | |
|---|---|---|
| 4,231,938 A | 11/1980 | Monaghan et al. |
| 4,342,767 A | 8/1982 | Albers-Schonberg et al. |
| 4,346,227 A | 8/1982 | Terahara et al. |
| 4,444,784 A | 4/1984 | Hoffman et al. |
| 4,582,915 A | 4/1986 | Sletzinger et al. |
| 4,681,893 A | 7/1987 | Roth |
| 4,820,850 A | 4/1989 | Verhoeven et al. |
| 4,976,967 A | 12/1990 | McClelland et al. |

(List continued on next page.)

FOREIGN PATENT DOCUMENTS

| | | |
|---|---|---|
| EP | 0 336 298 | 10/1989 |
| EP | 0 547 000 | 6/1993 |

(List continued on next page.)

OTHER PUBLICATIONS

Ito, et al., "Effects of Extensive and Poor Gastrointestinal Metabolism on the Pharmacodynamics of Pravastatin", Journal of Clinical Pharmacology, pp. 331–336, 1998.

Kantola, et al., "Effect of itraconazole on the pharmacokinetics of atorvastatin", Clinical Pharmacology & Technology, vol. 64, No. 1, pp. 58–65, 1998.

Kaufman, "Rate and equilibrium constants for acid–catalyzed lactone hydrolysis of HMG–CoA reductase inhibitors", International Journal of Pharmaceutics, pp. 97–106, 1990.

(List continued on next page.)

Primary Examiner—Thurman K. Page
Assistant Examiner—Humera N. Sheikh
(74) Attorney, Agent, or Firm—Carol S. Quagliato; Melvin Winokur

(57) ABSTRACT

The instant invention provides methods and pharmaceutical compositions for inhibiting HMG-CoA reductase, as well as for treating and/or reducing the risk for diseases and conditions affected by inhibition of HMG-CoA reductase, comprising orally administering a therapeutically effective amount of a compound selected from a dihydroxy open acid statin and a pharmaceutically acceptable salt or ester thereof in a delayed-release pharmaceutical dosage form to a patient in need of such treatment wherein substantial release of the compound from the dosage form is delayed until after passage of the dosage form through the stomach.

26 Claims, 4 Drawing Sheets

U.S. PATENT DOCUMENTS

| | | | |
|---|---|---|---|
| 4,997,658 A | 3/1991 | Alberts et al. | |
| 5,177,080 A | 1/1993 | Angerbauer et al. | |
| 5,223,415 A | 6/1993 | Conder et al. | |
| 5,225,202 A | 7/1993 | Hodges et al. | |
| 5,273,995 A | 12/1993 | Roth | |
| 5,354,772 A | 10/1994 | Kathawala | |
| 5,366,738 A | 11/1994 | Rork et al. | |
| 5,376,383 A * | 12/1994 | Alberts et al. | 424/473 |
| 5,686,104 A | 11/1997 | Mills et al. | |
| 5,882,682 A | 3/1999 | Rork et al. | |
| 5,916,595 A | 6/1999 | Chen et al. | |
| 6,331,316 B1 * | 12/2001 | Ullah et al. | 424/482 |

FOREIGN PATENT DOCUMENTS

| | | |
|---|---|---|
| EP | 0 547 000 A1 * | 6/1993 |
| WO | WO 97/03958 | 2/1997 |
| WO | WO 97/03959 | 2/1997 |
| WO | WO 97/23200 | 7/1997 |
| WO | WO 99/06035 | 7/1997 |
| WO | WO 99/06046 | 7/1998 |
| WO | WO 99/30692 | 6/1999 |
| WO | WO 99/47123 | 9/1999 |
| WO | WO 00/03696 | 1/2000 |
| WO | WO 00/21525 | 4/2000 |

OTHER PUBLICATIONS

Yalpani, "Cholesterol–lowering drugs", Chemistry & Industry, pp. 85–89, 1996.

Kearney, et al., "The Interconversion Kinetics, Equilibrium, and Solubilities of the Lactone and Hydroxyacid Forms of the HMG–CoA Reductase Inhibitior, CI–981", Pharmaceutical Research, vol. 10 pp. 1461–1465, 1993.

PR Newswire, Novartis Pharmaceuticals Corporation, Nov. 3, 1998.

The Physician's Desk Reference, 52nd Edition, 1998.

Maki et al., "Immunogenicity study of simvastatin and its dihydroxy open acid form", Oyo Yakuri/Pharmacometrics, vol. 39, No. 2, pp. 181–189, 1990.

Maki, E., et al., Immunogenicity study of simvastatin and its dihydroxy open acid form. Oyo Yakuri/Pharmacometrics 39 (2) 181–189 (1990).

Chemical Abstracts Registry No. 151006–19–8 (1998).
Chemical Abstracts Registry No. 151006–20–1 (1998).
Chemical Abstracts Registry No. 151006–21–2 (1998).
Chemical Abstracts Registry No. 151006–22–3 (1998).
Chemical Abstracts Registry No. 151006–23–4 (1998).
Chemical Abstracts Registry No. 151006–24–5(1998).
Chemical Abstracts Registry No. 151006–25–6 (1998).
Chemical Abstracts Registry No. 151006–26–7 (1998).
Chemical Abstracts Registry No. 101314–97–0 (1998).
Chemical Abstracts Registry No. 136733–85–2 (1998).
Chemical Abstracts Registry No. 139893–43–9 (1998).
Chemical Abstracts Registry No. 151006–16–5 (1998).
Chemical Abstracts Registry No. 151006–17–6 (1998).
Chemical Abstracts Registry No. 151006–18–7 (1998).

McClelland, et al., "Enhancement of 3–Hydroxy–3–methylglutaryl–Coenzyme A (HMG–CoA) Reductase Inhibitor Efficacy Through Administration of a Controlled–Porosity Osmotic Pump Dosage Form", Pharmacutical Research, vol. 8 pp. 873–876, 1991.

* cited by examiner

DIHYDROXY OPEN-ACID AND SALTS OF HMG-COA REDUCTASE INHIBITORS

This application is a continuation-in-part of U.S. Ser. No. 09/516,259, filed Feb. 29, 2000, which is CIP of Ser. No. 09/264,744, filed Mar. 9, 1999, which claims priority to provisional application U.S. Ser. No. 60/123,227, filed Mar. 8, 1999.

FIELD OF THE INVENTION

The instant invention relates to the use of dihydroxy open acid statins and salts and esters thereof, which are inhibitors of 3-hydroxy-3-methylglutaryl coenzyme A (HMG-CoA) reductase, in such a way so as to minimize their in vivo lactonization, and to a particular crystalline hydrated form of the calcium salt of dihydroxy open acid simvastatin referred to herein as compound I.

BACKGROUND OF THE INVENTION

It has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938), the first inhibitor of HMG-CoA reductase to become available for prescription in 1987, for the first time physicians were able to obtain comparatively large reductions in plasma cholesterol with very few adverse effects.

In addition to the natural fermentation products, mevastatin and lovastatin, there are now a variety of semi-synthetic and totally synthetic HMG-CoA reductase inhibitors, including simvastatin (ZOCOR®; see U.S. Pat. No. 4,444,784), pravastatin sodium salt (PRAVACHOL®; see U.S. Pat. No. 4,346,227), fluvastatin sodium salt (LESCOL®; see U.S. Pat. No. 5,354,772), atorvastatin calcium salt (LIPITOR®; see U.S. Pat. No. 5,273,995) and cerivastatin sodium salt (also known as rivastatin; see U.S. Pat. No. 5,177,080). The structural formulas of these and additional HMG-CoA reductase inhibitors, are described at page 87 of M. Yalpani, "Cholesterol Lowering Drugs", Chemistry & Industry, pp. 85–89 (Feb. 5, 1996). The HMG-CoA reductase inhibitors described above belong to a structural class of compounds which contain a moiety which can exist as either a 3-hydroxy lactone ring or as the corresponding ring opened dihydroxy open-acid, and are often referred to as "statins." An illustration of the lactone portion of a statin and its corresponding open-acid form is shown below.

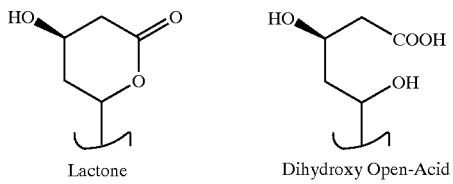

Lactone        Dihydroxy Open-Acid

Salts of the dihydroxy open-acid can be prepared, and in fact, as noted above, several of the marketed statins are administered as the dihydroxy open acid salt forms. Lovastatin and simvastatin are marketed worldwide in their lactonized form. Lovastatin is shown as structural formula II, and simvastatin is shown as structural formula III, below.

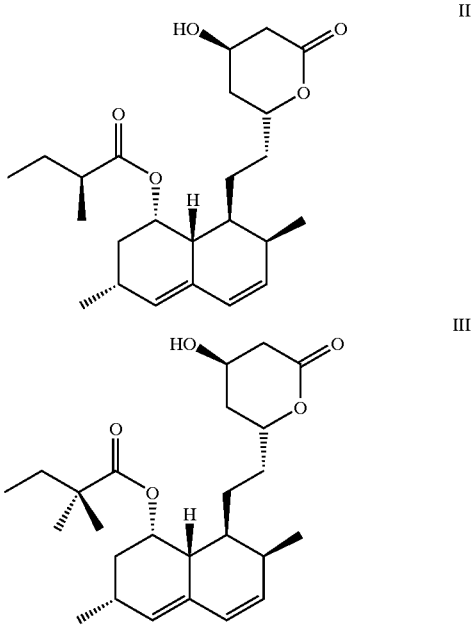

The lactonized forms of the statins are not active inhibitors of HMG-CoA reductase, but the dihydroxy open acid forms are. It is known that condensation of the dihydroxy open acid form of statins to the corresponding lactonized form occurs under acidic conditions, that is at about pH 4 or under. Therefore, due to the low gastric pH of the stomach, a statin conventionally administered by oral dosing in its lactone form will remain largely in its lactone form in the stomach. The vast majority of the drug will still be in the lactone form at the time of absorption from the intestine following oral dosing with the lactone. After absorption, the lactone enters the liver and it is in the hepatocytes that the lactone can be metabolized to the active open acid form, a reaction catalyzed by two hepatic esterases or "lactonases," one which is in the cytosolic and the other in the microsomal fraction. Once in the blood there is an additional plasma esterase which can also hydrolyze the lactone to the open acid. There may be some minimal chemical, i.e., non-enzymatic, hydrolysis that occurs in blood or in the liver; however, at the pH in blood and liver, there should not be any lactonization, i.e., conversion of open acid back to the lactone.

A statin conventionally administered by oral dosing in its dihydroxy open acid form or a pharmaceutically acceptable salt or ester thereof will tend to convert to its lactone form in the acidic environment of the stomach, so that a mixture of the open ring and the corresponding closed ring forms will co-exist there. For example, see M. J. Kaufman, International Journal of Pharmaceutics, 1990, 66(December 1), p. 97–106, which provides hydrolysis data that are used to simulate the extent of drug degradation that occurs in acidic gastric fluids following oral administration of several structurally related hypocholesterolemic agents, including simvastatin and lovastatin, and also see A. S. Kearney, et al., Pharmaceutical Research, 1993, 10(10), p. 1461–1465, which describes the interconversion kinetics and equilibrium of CI-981 (atorvastatin in its free acid form). Therefore, even after conventional oral dosing with a dihydroxy open acid statin or a salt or ester thereof, a mixture of the open acid and the corresponding lactone form of the drug could exist by the time of absorption from the intestine.

The preparation of the naturally occurring compound lovastatin and the semi-synthetic analog simvastatin leads to a mixture of the lactone and the open-ring dihydroxy acid forms. Several procedures have been published describing ways to make simvastatin from lovastatin, and most proceed through a lactone ring opening step at some point in the process and sometimes formation of a salt at the resulting carboxy acid, and end with a ring-closing step in order to make the final simvastatin product. For example, U.S. Pat. No. 4,820,850 describes a process for making simvastatin which involves opening the lactone ring of lovastatin and forming an alkyl-amide at the resulting carboxy acid, followed by protection of the two hydroxy groups and methylation of the 8' acyl sidechain. After the methylation step, the hydroxy protecting groups are removed, the amide is hydrolyzed to the free acid and an ammonium salt of the free acid is formed, followed by a step to re-lactonize the ring. In U.S. Pat. No. 4,444,784, the 8'-acyl sidechain of lovastatin is removed and the lactone ring opened in the first step, followed by re-lactonization of the ring and protection of its hydroxy group. Next, the 8' position is acylated to introduce the simvastatin sidechain and a deprotection step is performed to obtain the simvastatin final product. In another process disclosed in U.S. Pat. No. 4,582,915, the potassium salt of the ring opened form of lovastatin is methylated at the 8' acyl sidechain, the free acid is then re-generated, and the dihydroxy open acid moiety is re-lactonized.

Since becoming available, millions of doses of simvastatin have been administered and these drugs have developed an excellent safety record. However, as noted in the Physician's Desk Reference (PDR), in rare instances myopathy has been associated with the use of all statins, including simvastatin. The mechanism for statin-related myopathy is currently poorly understood. It is also known that many drugs, including certain statins such as simvastatin, are metabolized in the liver and intestine by the cytochrome P450 3A4 (CYP 3A4) enzyme system. As also noted in the PDR, there are adverse drug interaction concerns if a potent inhibitor of CYP3A4, such as itraconazole, and a CYP3A4-metabolized statin are used together, and some cases of myopathy were found to have occurred in patients taking such a drug combination. Simvastatin has been administered to over 20 million patients worldwide in the past 11 years and has been demonstrated to be remarkably safe. However, the very low risk of myopathy is substantially increased when simvastatin is given together with potent inhibitors of CYP3A4 While the overall safety record for simvastatin is exceptional, it would be desirable to further optimize its safety profile by reducing the potential for drug interactions with inhibitors of CYP3A4. It would also be desirable to further reduce the already low rate of occurrence of myopathy associated with the use of all statins. Statins are among the most widely used drugs in the world, and therefor the benefit of any further optimization of their safety profile would be significant.

SUMMARY OF THE INVENTION

One object of this invention is to minimize or eliminate the in vivo lactonization of a dihydroxy open-acid statin. For oral administration, the dihydroxy open-acid statin or a pharmaceutically acceptable salt or ester thereof is to be administered so as to minimize formation of lactonized statin and thereby minimize the amount of lactonized statin that is absorbed from the intestine while maximizing the amount of dihydroxy open-acid statin that is absorbed from the intestine.

Accordingly, this invention involves a method of inhibiting HMG-CoA reductase with an effective inhibitory amount of an orally dosed statin comprising delivering at least 90% of the dosed statin in its dihydroxy open acid form to the intestinal mucosa of a patient in need of such treatment.

The instant invention further provides a method for inhibiting HMG-CoA reductase, as well as for treating and/or reducing the risk for diseases and conditions affected by inhibition of HMG-CoA reductase, comprising orally administering a therapeutically effective amount of a compound selected from a dihydroxy open acid statin and a pharmaceutically acceptable salt or ester thereof in a delayed-release pharmaceutical dosage form to a patient in need of such treatment wherein substantial release of the compound from the dosage form is delayed until after passage of the dosage form through the stomach.

One embodiment of the first object is to provide the above-described method wherein the delayed-release pharmaceutical dosage form is a gel extrusion module (GEM) drug delivery device.

Another embodiment of the first object is to provide the above-described method wherein the delayed-release pharmaceutical dosage form is an enterically coated pharmaceutical dosage form. An additional aspect of this embodiment is to provide the above-described method wherein the delayed-release pharmaceutical dosage form is selected from an enterically coated rapid-release pharmaceutical dosage form and an enterically coated time controlled-release pharmaceutical dosage form. Yet another aspect of this embodiment is to provide the above-described method wherein the delayed-release pharmaceutical dosage form is an enterically coated gel extrusion module (GEM) drug delivery device.

The compound used for the above-described object and embodiments may particularly be dihydroxy open acid simvastatin and the pharmaceutically acceptable salts thereof, and more particularly a pharmaceutically acceptable salt thereof.

A second object of the instant invention is to provide novel HMG-CoA reductase inhibitors which are crystalline hydrated forms of the calcium salt of dihydroxy open acid simvastatin, and particularly the compound referred to herein as compound I.

Additional objects are to provide the use of the crystalline hydrated forms of the calcium salt of dihydroxy open acid simvastatin, particularly compound I, for inhibiting HMG-CoA reductase, as well as for treating and/or reducing the risk for diseases and conditions affected by inhibition of HMG-CoA reductase, and also to provide pharmaceutical formulations, including conventional rapid-release, delayed-release and time controlled-release formulations, including the GEM drug delivery device and enterically coated dosage forms, that can be used with the compounds. A further embodiment is to provide a composition and method for improving the long-term stability of a formulated drug product containing compound I by enterically coating a core tablet comprised of compound I with an enteric coating, particularly SURETERIC WHITE®. A further object is to provide a process for making compound I. Additional objects will be evident from the following detailed description.

DETAILED DESCRIPTION OF THE INVENTION

Figure 1:
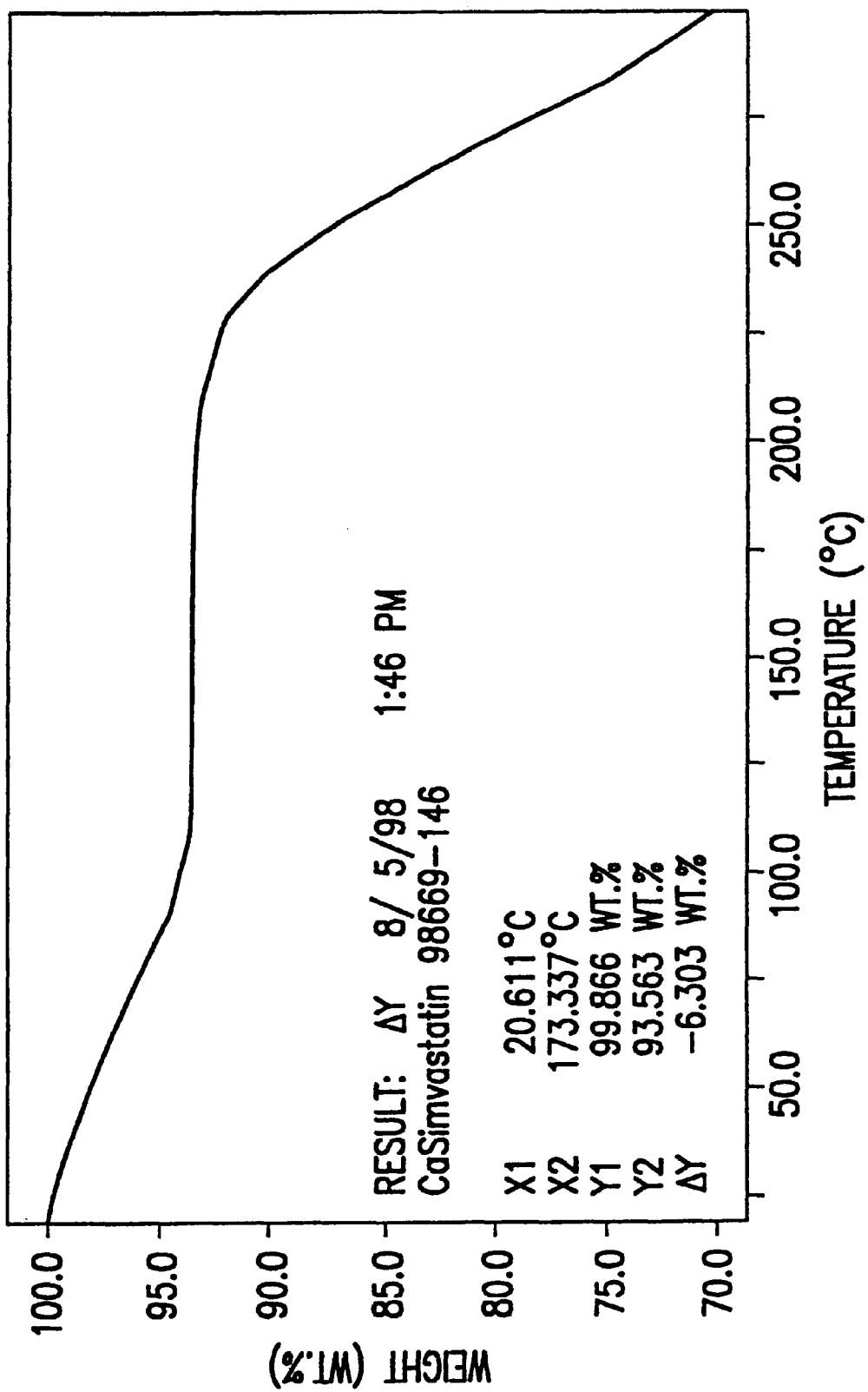
FIG. 1 is a thermogravimetry (TG) weight loss curve for compound I obtained under a nitrogen flow at a heating rate of 10° C./minute.

Applicants have now discovered that dihydroxy open acid statins may be less reliant on CYP3A4 metabolism than their closed ring lactonized counterparts. The instant invention involves methods and pharmaceutical compositions for orally administering open-ring dihydroxy open acid statins and salts and esters thereof, which are HMG-CoA reductase inhibitors, in such a way so as to minimize conversion to their lactonized counterparts. This allows for delivery of a dihydroxy open acid statin without its lactone counterpart directly to the absorptive mucosa of the small intestine thus allowing for absorption of the open acid statin into the portal circulation, penetration by active open acid statin into hepatocytes to achieve enhanced efficacy, and systemic exposure consisting of open acid moieties. More particularly, delayed-release of an orally administered dihydroxy open acid statin or a pharmaceutically acceptable salt or ester thereof, for example dihydroxy open acid simvastatin or a salt thereof, until after passage through the stomach reduces the amount of lactone formed and absorbed in the body. Maintaining the statin in its open acid form in the body thereby reduces the potential for drug interactions between statins whose metabolism is CYP3A4-mediated and other active agents which inhibit the CYP3A4 enzymatic pathway, and also can provide enhanced efficacy. Moreover, maintaining the statin in its open acid form in the body may have additional clinical benefits for all statins, even for those statins that are not significantly metabolized by the CYP3A4 enzymatic pathway.

In addition, a novel crystalline hydrated form of the calcium salt of dihydroxy open acid simvastatin has now been discovered to be a pharmaceutically suitable salt form having desirable physical properties for formulation into an anti-hypercholesterolemic drug composition.

The term "statin(s)" as used herein is intended to be defined as inhibitors of HMG-CoA reductase which belong to a structural class of compounds that contain a moiety which can exist as either a 3-hydroxy lactone ring or as the corresponding ring opened dihydroxy open acid, wherein the lactone portion of the statin and its corresponding dihydroxy open-acid form is shown below.

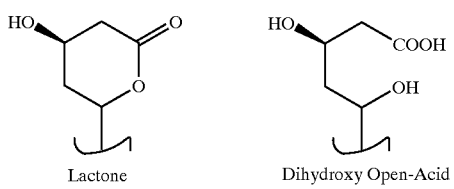

Lactone         Dihydroxy Open-Acid

All hydrates, solvates and polymorphic crystalline forms of HMG-CoA reductase inhibitors having the above-described lactone/dihydroxy open acid moiety are included within the scope of the term "statin(s)". Pharmaceutically acceptable salts and esters of the dihydroxy open-acid statins are included within the scope of the term "statin(s)".

Statins inhibit HMG-CoA reductase in their dihydroxy open acid form. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33.

The term "dihydroxy open acid statin(s)" is intended to be defined as statins which contain the dihydroxy open acid moiety, including pharmaceutically acceptable salts and esters thereof. The phrases "dihydroxy open acid statin(s)" and "dihydroxy open acid statin(s) and the pharmaceutically acceptable salts and esters thereof" are used interchangeably herein and are both intended to encompass the open acid and salt and ester forms of the open acid of the statin, unless otherwise indicated. All hydrates, solvates and polymorphic crystalline forms are encompassed within the the scope of the term "dihydroxy open acid statin(s)."

In the broadest embodiment, any dihydroxy open acid statin or a pharmaceutically acceptable salt or ester thereof may be used with the present invention. Examples of dihydroxy open acid statins that may be used with the present invention include but are not limited to the dihydroxy open acid forms and pharmaceutically acceptable salts and esters thereof of: lovastatin (see U.S. Pat. No. 4,342,767); simvastatin (see U.S. Pat. No. 4,444,784), pravastatin, particularly the sodium salt thereof; fluvastatin particularly the sodium salt thereof; atorvastatin, particularly the calcium salt thereof; cerivastatin, particularly the sodium salt thereof, nisvastatin also referred to as NK-104 (see PCT international publication number WO 97/23200) and ZD-4522 (see U.S. Pat. No. 5,260,440, and Drugs of the Future, 1999, 24(5), pp. 511–513).

In a narrower embodiment, any dihydroxy open acid statin or a pharmaceutically acceptable salt or ester thereof may be used with the present invention, such as those listed above, provided the statin is not pravastatin or fluvastatin. In a class of this embodiment, the open acid statin includes dihydroxy open acid lovastatin, simvastatin, atorvastatin, cerivastatin, nisvastatin (also known as NK-104) and pharmaceutically acceptable salts thereof. Pharmaceutically acceptable salts of dihydroxy open acid simvastatin, particularly the ammonium and calcium salt forms thereof, are preferred for use in the methods and compositions of this invention. More particularly, the calcium salt of dihydroxy open acid simvastatin includes the crystalline hydrated forms of the calcium salt of dihydroxy open acid simvastatin, and more particularly the hydrated calcium salt of dihydroxy open acid simvastatin referred to herein as compound I.

Herein, the term "pharmaceutically acceptable salts" shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, morpholine, 2,4,4-trimethyl-2-pentamine and tris(hydroxymethyl)aminomethane. Pharmaceutically acceptable esters at thecarboxylic acid group-can be made by treating a dihydroxy open acid statin with an alcohol. Examples of pharmaceutically acceptable esters of dihydroxy open acid statins include, but are not limited to, —$C_{1-4}$ alkyl and —$C_{1-4}$ alkyl substituted with phenyl-, dimethylamino-, and acetylamino. "$C_{1-4}$ alkyl" herein includes straight or branched aliphatic chains containing from 1 to 4 carbon atoms, for example methyl, ethyl, n-propyl, n-butyl, iso-propyl, sec-butyl and tert-butyl.

The instant invention involves methods and pharmaceutical compositions for orally administering open-ring dihydroxy open acid statins and salts and esters thereof, which are HMIG-CoA reductase inhibitors, in such a way so as to minimize conversion to their lactonized counterparts. This allows for delivery of a dihydroxy open acid statin without its lactone counterpart directly to the absorptive mucosa of the small intestine thus allowing for absorption of the open acid statin into the portal circulation, penetration by active open acid statin into hepatocytes to achieve enhanced efficacy, and systemic exposure consisting of open acid moieties. More particularly, delayed-release of an orally administered dihydroxy open acid statin or a pharmaceutically acceptable salt or ester thereof, for example dihydroxy open acid simvastatin or a salt thereof, until after passage through the stomach reduces the amount of lactone formed and absorbed in the body. Maintaining the statin in its open acid form in the body thereby reduces the potential for drug interactions between statins whose metabolism is CYP3A4-mediated and other active agents which inhibit the CYP3A4 enzymatic pathway, and also can provide enhanced efficacy. Administering a statin in its open acid form in such a way so as to minimize conversion to its lactonized counterpart, for example by using an oral delayed release dosage form, should reduce the potential for drug interaction compared to the conventional administration of an open acid statin or its lactonized counterpart, for example by using an oral rapid release dosage form.

An object of this invention is to provide methods for reducing the amount of lactonized statin formed and absorbed in the body after oral administration of a dihydroxy open acid statin in order to achieve enhanced clinical benefits. A way to achieve this is to administer the dihydroxy open acid statin in a delayed-release pharmaceutical dosage form. A delayed-release pharmaceutical dosage form as defined herein is an orally administerable pharmaceutical dosage form or device that does not release a substantial amount of the active compound, i.e., the dihydroxy open-acid statin, until after the dosage form has passed through the stomach. Therefore, substantial release of the active compound would initially occur after entry into the duodenum. By "substantial release," it is intended that 90% or more by weight of the active compound in the delayed-release dosage form is released after entry into the duodenum, and that 10% or less by weight of the active compound in the delayed-release dosage form is released in the stomach, i.e., the geometric mean ratio of the plasma AUC (area under the curve) of active vs. total HMG-CoA reductase inhibitory activity will be greater than or equal to 90%. Particularly, the amount of active compound released in the stomach before entry into the duodenum is 5% or less by weight, i.e., the geometric mean ratio of the plasma AUC of active vs. total HMG-CoA reductase inhibitory activity will be greater than or equal to 95%, and more particularly the amount of active compound released in the stomach before entry into the duodenum is 1% or less by weight, i.e., the geometric mean ratio of the plasma AUC of active vs. total HMG-CoA reductase inhibitory activity will be greater than or equal to 99%.

It is to be understood that metabolism of the dihydroxy open acid statins will occur, primarily in the liver, after orally dosing in a delayed-release dosage form. However, since lactonization of the dihydroxy open acid statin would have been substantially avoided by use of a delayed release dosage form, the active and inactive metabolites that are formed will also be in the dihydroxy open acid form. In essence, if the dihydroxy open acid statin is administered in a delayed release dosage form, the internal exposure to lactonized parent compound and also to lactonized active and inactive metabolites will be minimized.

One example of a suitable delayed-release dosage form is a pH-dependent enterically coated dosage form. The enteric coating will not dissolve in the acidic gastric environment, but will dissolve in the higher pH environment of the duodenum. An enterically coated dosage form will therefore not permit release of any significant amount of the active compound from the dosage form in the stomach, but once the enteric coating dissolves in the duodenum, the active compound will be released. Suitable compositions for enteric coatings that can be used with the present invention are known to those of ordinary skill in the pharmaceutical arts; for example, see L. Lachman, The Theory and Practice of Industrial Pharmacy, 3rd Ed., H. Lieberrnann and J. Kanig contributors (Lea & Febiger, 1986). An example of a suitable enteric coating includes but is not limited to SURETERIC WHITE® sold by Colorcon which is composed of polyvinyl acetate phthalate, titanium dioxide, talc, colloidal silicon dioxide, triethyl citrate, Macrogol/PEG 4000 (a type of polyethylene glycol), sodium bicarbonate, purfied stearic acid, and sodium alginate. Many other suitable enteric coating materials are commercially available and are known in the art and include but are not limited to coatings comprised of any of the following polymers: polyvinyl acetate phthalate (PVAP), hydroxypropyl methylcellulose phthalate (HPMCP), hydroxypropyl methylcellulose acetate succinate (HPMCAS), cellulose acetate trimellitate (CAT), cellulose acetate phthalate (CAP), polymethacrylates and shellac. The polymethacrylates are a class of polymers used in pharmaceutical coatings for sustained or controlled release. The EUDRAGITs® are a particular brand of products based upon this polymer class and are available from Rohm Pharma GmbH. EUDRAGIT L® (methacrylic acid/ethyl acrylate) is one type of marketed enteric polymer, and is available as a powder for organic or aqueous dispersion, or as a pseudolatex aqueous dispersion. EUDRAGIT S® is another example in this class which is soluble at slightly more basic conditions than EUDRAGIT L®.

Most of the materials used for enteric coatings are prepared as solutions or suspensions prior to coating. In addition to the polymer, other materials are often added to these formulations to improve coating integrity or processability. For example, other materials commonly used in filmcoating formulations include: plasticizers, which aid in film formation and improve the flexibility of the final film, making it less susceptible to cracking; antitacking agents, which prevent the product from agglomerating during the coating process, and/or opacifiers, which may improve the elegance of the dosage form, or provide additional protection from the environment.

The vehicles used to deliver these formulations are typically aqueous or organic, or may be mixtures of solvents. Equipment used to process formulations containing organic solvents often require a solvent recovery system in order to prevent release of solvent vapors to the atmosphere, as well as additional safety and monitoring equipment to minimize the potential for explosivity. Because of these environmental concerns associated with organic solvents, aqueous solvent methods are preferred.

The coating process of pharmaceutical dosage forms, such as powders, granules, pellets, or tablets, typically takes place in one of several types of coating equipment, including pan coaters, fluidized bed coaters, or continuous coaters. The coating of tablets usually takes place in pan coaters although tablets are often coated in a fluidized bed if a solvent-based coating is used. The coating of powders, granules, or pellets is often performed in fluidized bed apparatus. However, the various types of coating equipment can be used to coat most pharmaceutical dosage forms, either directly or with limited modification.

Coating conditions vary widely, and depend primarily on the process, substrate, and coating formulation. Spray rate and coating temperature are targeted as two key parameters to control in order to obtain an acceptable product and process. There is often a strong interdependence between spray rate and coating temperature, and both must be considered during process development and optimization. The processing conditions are often dictated by the type of polymer used in the coating formulation, but may also depend upon the characteristics of the substrate. For example, the temperature at which the active material (or other components) in the core begins to degrade may limit the maximum coating temperature. However, a certain minimum temperature may be necessary to form a continuous film.

The level of coating applied to a dosage form is an important consideration. In the case of certain coatings, for example, a minimum amount of coating is needed to provide sufficient resistance to acid or environmental degradation, while beyond a desired coating level dissolution of the drug may be delayed or prevented altogether. The key in these formulations is to provide enough coating to protect the dosage form, but not so much that the performance of the dosage form is affected.

Additional coatings employed in the preparation of the dosage form, such as those used to provide an elegant, aesthetically pleasing final product or for other purposes, may be applied before or after, or before and after, application of the enteric coating.

Suitable enterically coated pharmaceutical dosage forms for use with this invention include enterically coated conventional rapid-release (also referred to as immediate-release) pharmaceutical dosage forms wherein the drug is relatively rapidly released once the enteric coating is breached, and enterically coated time-controlled release dosage forms such as but not limited to an enterically coated GEM delivery device, described below. Time controlled-release dosage forms are also well known in the pharmaceutical art, and are designed so as to slowly release the active compound in the body over a period of time, for example over a period of from about 6 to 24 hours. Use of an enteric coated time controlled-release dosage form is preferred with more potent dosage amounts of a dihydroxy open acid statin so as to lower the systemic exposure to the active statin. Whether the dosage form is an enterically coated rapid-release or time-controlled release dosage form, the enteric coating will prevent release of any substantial amount of the active compound from the dosage form in the stomach.

Enterically coated pharmaceutical dosage forms also include but are not limited to those wherein the dosage forms or unit is comprised of the dihydroxy open acid statin in a tablet, capsule or the like that is surrounded by an enteric overcoating, and those wherein the dosage form or unit is a tablet, capsule or the like comprised of enterically coated granules of the dihydroxy open acid statin. Where the dosage form is surrounded by an enteric overcoat, the enteric coating may be the outer-most external coating on the dosage form, or there may be one or more additional finish coatings applied over the enteric coat. In a more limited embodiment, when the delayed-release dosage unit contains enterically coated granules of the drug, the drug is selected from the dihydroxy open-acid form of lovastatin and simvastatin and the pharmaceutically acceptable salt and ester forms thereof, and is more preferably a salt of dihydroxy open acid simvastatin, and most preferably the calcium or ammonium salt thereof. In an alternative embodiment, any dihydroxy open acid statin or pharmaceutically acceptable salt or ester thereof may be used with the present invention, such as those described herein, provided that the statin is not dosed in a single pharmaceutical dosage form or unit comprised of enteric coated granules of the statin and enteric coated or non-enteric coated granules of aspirin.

Furthermore, compound I is challenging to stabilize in a formulated drug product. Surprisingly, stability of the core tablet comprised of compound I as the active agent is greatly improved by addition of a polymeric coating, particularly a polymeric coating comprised of polyvinyl acetate phthalate (PVAP), and more particularly the enteric polymeric coating SURETERIC WHITE. The use of the PVAP-based coating has unexpectedly been found to inhibit the degradation of the active agent in the formulated drug product, thereby providing enhanced long term stability of the formulated drug product. A sub-coat may optionally be applied to the core tablet prior to application of the polymeric coating to aid in adhesion of the polymeric coating. A sub-coat example includes, but is not limited to, one comprised of a mixture of 50% hydroxypropyl cellulose/50% hydroxypropyl methyl cellulose (i.e., a 1:1 ratio hydroxypropyl cellulose:hydroxypropyl methyl cellulose mixture). The sub-coat may also contain additional components such as a coloring agent, for example titanium dioxide. The polymeric coating is applied to the tablet over the sub-coat, for example by a spray coating process. An optional additional top-coat can be applied over the polymeric coating for aesthetic or other purposes; for example, the top-coat can be the same or similar composition as the sub-coat and can be used to add color or to aid in the application of other markings on the finished tablet. The polymeric coating, particularly SURETERIC WHITE®, can be applied to the tablet in an amount and thickness to achieve the desired stability enhancement while also taking into account the desired in vivo release performance associated with the pH sensitive characteristics of the enteric coating. For example, SURETERIC WHITE® can be applied in a range from, but not limited to, 5% to 15% tablet weight gain, which corresponds to about 50 to 150 micron coating thickness, and particularly about 10% tablet weight gain.

An example of a delayed-release dosage form that also functions as a time controlled-release dosage form is described in U.S. Pat. No. 5,366,738, herein incorporated by reference in its entirety. The controlled-release drug delivery device described in U.S. Pat. No. 5,366,738 is known as a gel extrusion module (GEM) delivery device. The GEM device is a drug delivery device for the controlled in situ production and release of a dispersion containing a beneficial agent such as a pharmaceutical drug comprising:

(A) a compressed core prepared from an admixture comprising:
(i) a therapeutically effective amount of the beneficial agent; and
(ii) a polymer which upon hydration forms gelatinous microscopic particles; and (B) a water insoluble, water impermeable polymeric coating comprising a polymer and a plasticizer, which surrounds and adheres to the core, the coating having a plurality of formed apertures exposing between about 1 and about 75% of the core surface;
and wherein the release rate of the beneficial agent from the device is a function of the number and size of the apertures.

In the GEM device, the polymer inside the compressed core is preferably selected from sodium polyacrylate, carboxypolymethylenes and the pharmaceutically acceptable salts thereof such as a sodium salt, wherein the carboxypolymethylenes are prepared from acrylic acid crosslinked with allylethers of sucrose or pentaerythritol, and more preferably it is selected from carboxypolymethylenes prepared from acrylic acid crosslinked with allylethers of sucrose or pentaerythritol, and the pharmaceutically acceptable salts thereof. Most preferably, CARBOPOL® 974P and pharmaceutically acceptable salts thereof, particularly the sodium salt, is used as the polymer inside the compressed core. In addition, the compressed core may also contain one or more polymer hydration modulating agents, antioxidants, lubricants, fillers and excipients. An optional subcoating may be applied to the compressed core prior to application of the water insoluble coating as an aid in the manufacturing process. The subcoating may be comprised of, for example, hydroxypropyl cellulose and hydroxypropylmethylcellulose. Additional coatings may be applied for aesthetic or functional purposes.

The water insoluble, water impermeable polymeric coating is preferably comprised of (1) a polymer selected from polyvinyl chloride, cellulose acetate, cellulose acetate butyrate, ethylcellulose and combinations of these polymers; and (2) a plasticizer selected from diethylphthalate, dibutylsebacate and triethylcitrate. More preferably, the polymeric coating is comprised of cellulose acetate butyrate and triethyl citrate. The GEM device does not function as an osmotic drug delivery device, hence the release function of the device depends on passage of fluids from the external environment of the body to the internal environment of the compressed core through the formed apertures. It is intended that the terms "water insoluble, water impermeable" used to describe the polymeric coating define a coating which is essentially water insoluble and water impermeable, meaning that the polymeric coating allows minimal to no passage of water through the coating from the external environment of the body to the internal environment of the compressed core, except for the fluid passage that occurs through the drilled apertures, during the period of time the drug is being released from the GEM device in the body. Any minimal amount of water that does pass through the water insoluble, water impermeable polymeric coating is insubstantial and does not significantly contribute to the function of the GEM device, i.e. the release rate of the drug through the apertures. Rather the release rate of the drug from the GEM device is primarily a function of the number and size of the apertures on the device.

For an elegant, aesthetically pleasing final product, an outter finish coat may finally be applied to the GEM delivery device containing colorants, waxes, and the like. The GEM device can also be enterically coated, either before or after the application of additional finish coatings. Even without enteric coating, extrusion of the polymer which carries the drug out from inside the compressed core of the GEM device does not occur to a substantial extent in the acidic pH of the stomach, therefore substantial release of the drug should not occur in the stomach. Further details and examples of the GEM delivery device are described in U.S. Pat. No. 5,366,738. The compound employed with the GEM device may particularly be a pharmaceutically acceptable salt of dihydroxy open acid simvastatin, and more particularly the ammonium salt of dihydroxy open acid simvastatin.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of HMG-CoA reductase.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL (low density lipoprotein) cholesterol lowering desired; the dosage a patient receives may also be titrated over time in order to reach a target LDL level. The dosage regimen utilizing a dihydroxy open acid statin is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

The novel compounds of this invention are the crystalline hydrated forms of the calcium salt of dihydroxy open acid simvastatin. A particular crystalline hydrated calcium salt of dihydroxy open acid simvastatin is the one having an x-ray powder diffraction (XRPD) pattern obtained using CuKα radiation characterized by reflections at d-spacings of 30.7, 24.6, 15.9, 11.2, 8.58, 7.31, 6.74, 6.06, 5.35, 5.09, 4.93, 4.60, 3.93, 3.84, 3.67, 3.51 and 3.28 Å. For convenience, the crystalline hydrated form of the calcium salt of dihydroxy open acid simvastatin having the above-defined XRPD pattern will also be referred to herein as compound I. Compound I can be represented two-dimensionally as a hydrated form of the following structural formula Ia:

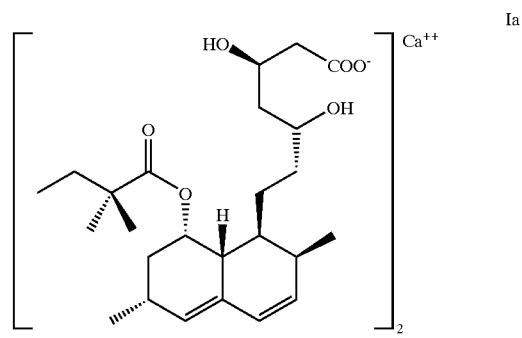

In addition to the XRPD pattern described above, compound I of the instant invention is further characterized by the thermogravimetry (TG) curve shown in FIG. I. The TG curve for compound I was obtained under a nitrogen flow at a heating rate of 10° C./minute and is characterized by a 6.3% weight loss from ambient room temperature to a stable weight loss plateau at about 175° C. Additional weight losses due to the onset of decomposition of the compound are observed above about 190° C.

Figure 2:
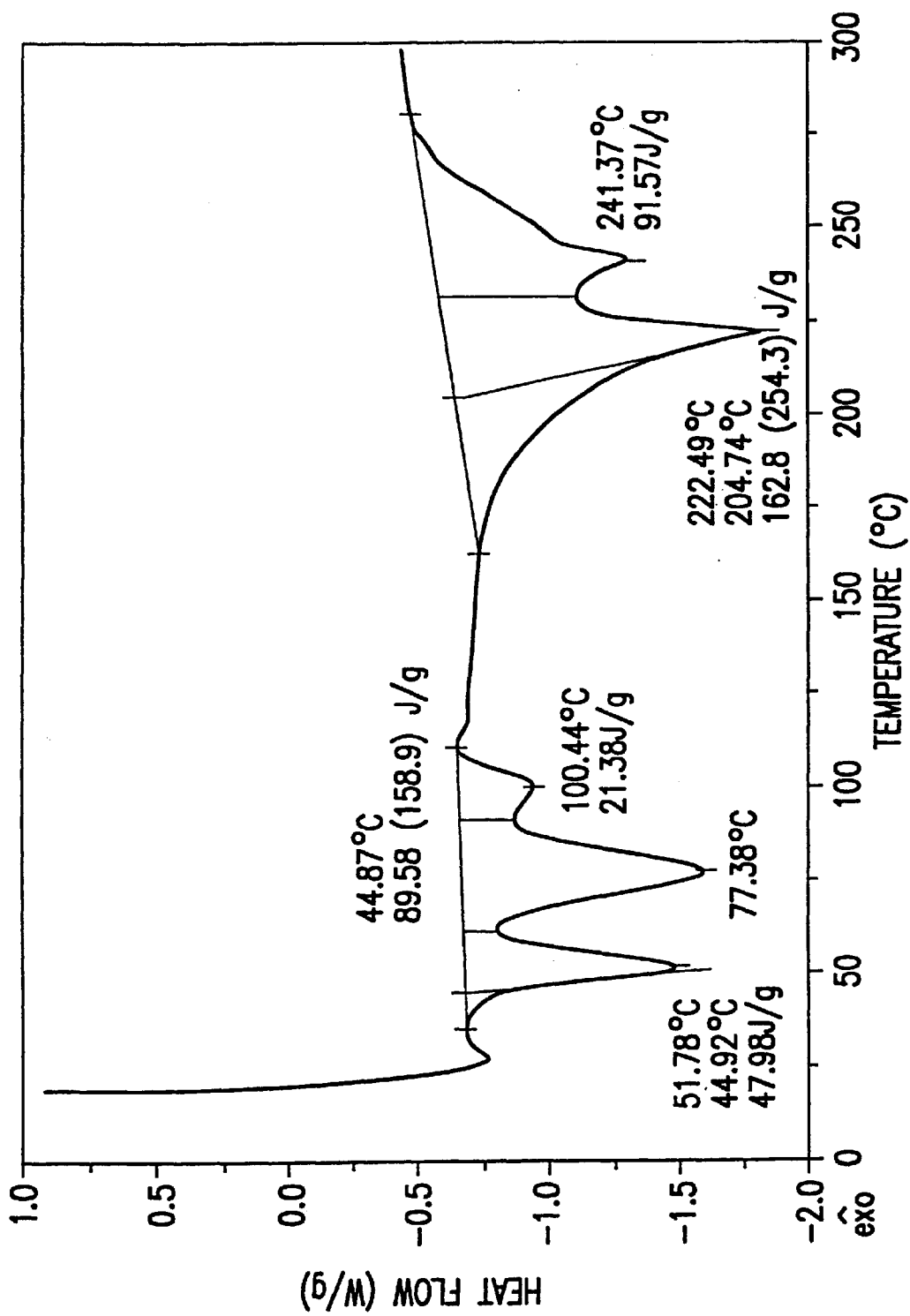
FIG. 2 is a differential scanning calorimetry (DSC) curve for compound I obtained under a nitrogen flow bubbled through 16.0° C. water at a heating rate of 10° C./minute in an open cup.
Figure 3:
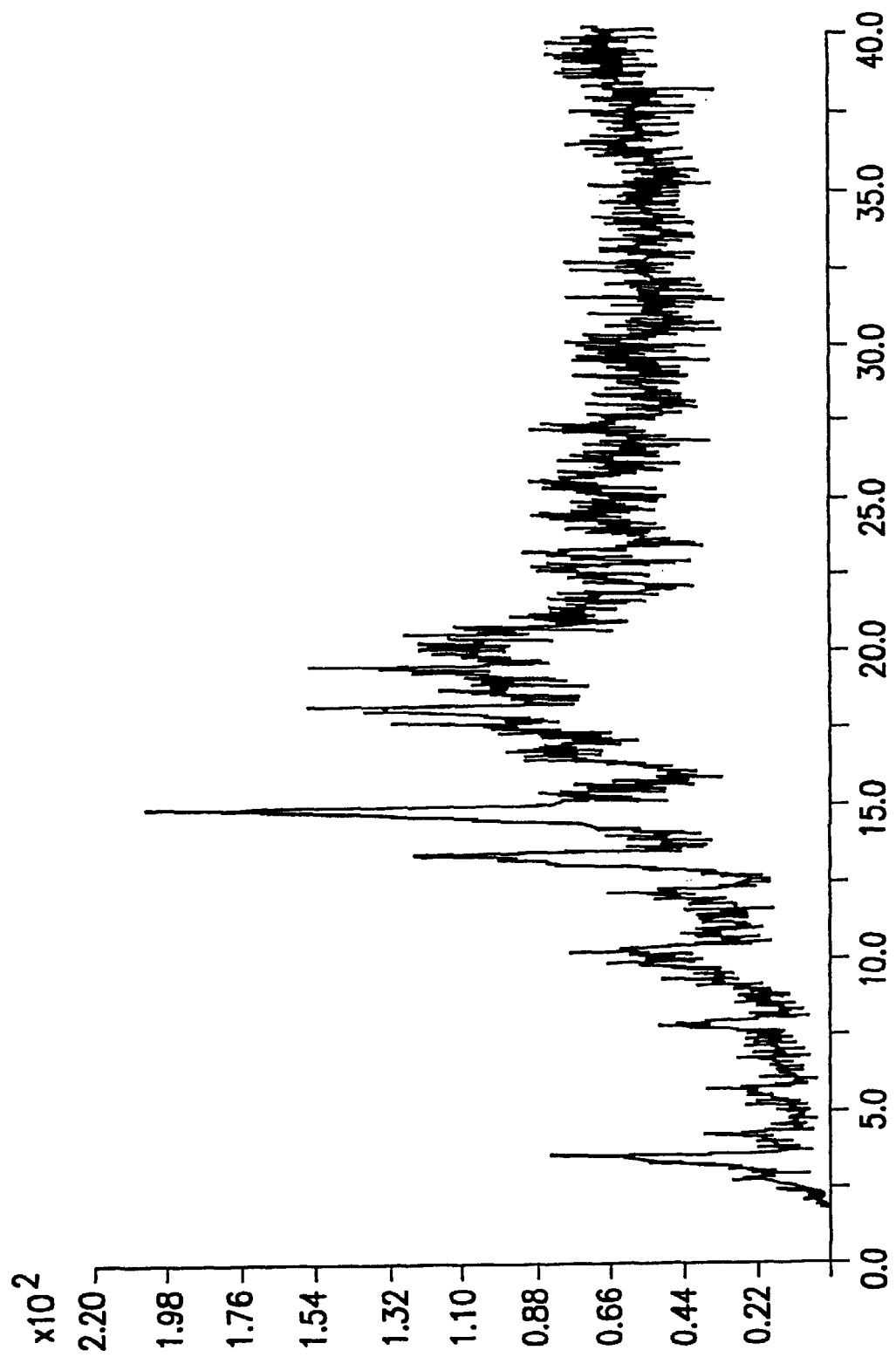
FIG. 3 is an x-ray powder diffraction (XRPD) pattern for compound I. The XRPD pattern was obtained using CuKα radiation. The ordinate or Y-axis is x-ray intensity (cpm) and the abscissa or X-axis is the angle two-theta (2θ) in degrees.

Compound I is still further characterized by the differential scanning calorimetry (DSC) curve shown in FIG. 2. The DSC curve for compound I was obtained under a nitrogen flow bubbled through 16.0° C. water at a heating rate of 10° C./minute in an open cup, and is characterized by three lower temperature endotherms with peak temperatures of 52, 77 and 100° C. and associated heats of 48, 90 and 21 J/g, respectively, and two higher temperature endotherms due to decomposition with peak temperatures of 222 and 241° C. and associated heats of 163 and 92 J/g.

Compound I of the instant invention is still further characterized by the $^1$H nuclear magnetic resonance (NMR) spectral data, $^{13}$C NMR and mass spectral (MS) data as given in Example 1 herein.

Figure 4:
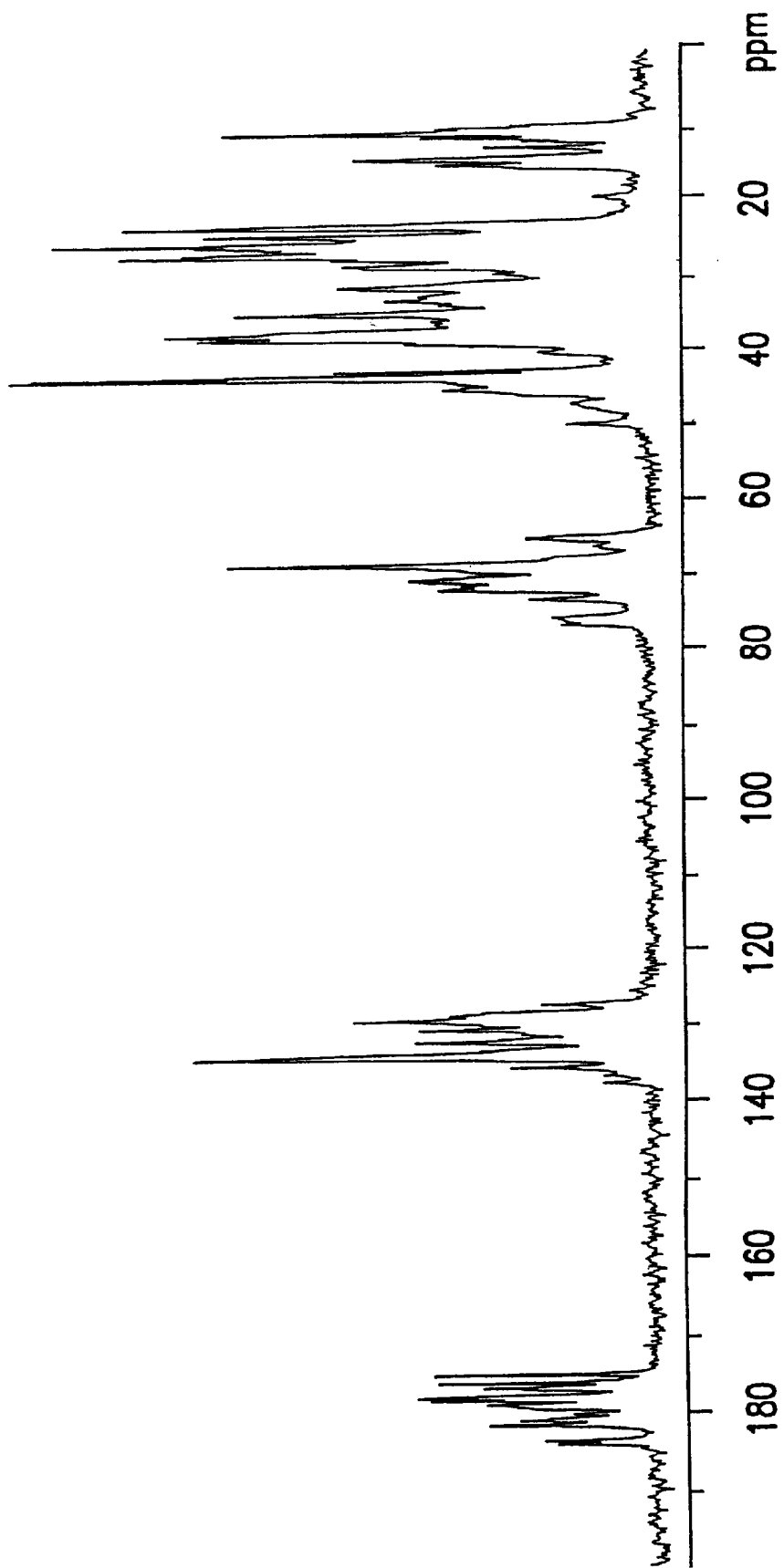
FIG. 4 is a solid-state $^{13}$C nuclear magnetic resonance spectrum for Compound I.

Compound I is also characterized by the solid-state $^{13}$C nuclear magnetic resonance spectrum shown in FIG. 4, which was completed using a Bruker DSX 400WB NMR system operating at 100.6 MHz for $^{13}$C and 400.1 MHz for $^1$H using a Bruker MAS 400WB BL7 double-resonance probe with a spinning module housing a 7 mm zirconia rotor with Kel-f end caps. The solid-state $^{13}$C nuclear magnetic resonance (NMR) spectrum was acquired using cross polarization (CP), magic-angle spinning (MAS), and high-power (~59 kHz) decoupling with variable-amplitude cross-polarization and total sideband suppression. Proton and carbon 90° pulse widths were 4.25 µsec with a contact time of 2.0 msec. The sample was spun at 7.0 kHz and a total of 1024 scans were collected for the spectrum with a recycle delay of 3.0 seconds. A line broadening of 10 Hz was applied to the spectrum before FT was performed. Chemical shifts are reported on the TMS scale using the carbonyl carbon of glycine (176.03 ppm) as a secondary reference.

In the methods of treatment and prophylaxis described herein, as well as the pharmaceutical compositions and medicaments, a dihydroxy open acid statin or a pharmaceutically acceptable salt or ester thereof is employed. Preferably the compound employed is a pharmaceutically acceptable salt of a dihydroxy open acid statin, more preferably it is a pharmaceutically acceptable salt of dihydroxy open acid simvastatin such as an ammonium salt or calcium salt, and particularly a crystalline hydrated form of the calcium salt of dihydroxy open acid simvastatin such as compound I. All hydrates, solvates and polymorphic crystalline forms of the above-described compounds and their use are encompassed within scope of the instant invention.

The instant invention provides methods for inhibiting HMG-CoA reductase, and for treating lipid disorders including hypercholesterolemia, hypertriglyceridemia and combined hyperlipidemia, comprising administering a therapeutically effective amount of a dihydroxy open acid statin to a person in need of such treatment. Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a dihydroxy open acid statin to a mammal who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A dihydroxy open acid statin may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a dihydroxy open acid statin to a patient at risk for such an event. The patient may or may not have atherosclerotic disease at the time of administration, or may be at risk for developing it.

The instant invention also provides a method for preventing and/or treating inflammatory diseases or disorders alone or in conjunction with the treatment of conditions described above, comprising the administration of a dihydroxy open-acid statin to a patient in need of such treatment. This includes, for example, the treatment of inflammatory conditions susceptible to treatment with a non-steroidal anti-inflammatory agent, arthritis including rheumatoid arthritis, and degenerative joint diseases (osteoarthritis), dementia, Alzheimer's disease, multiple sclerosis, inflammatory bowel disease, asthma, psoriasis, systemic lupus erythematosis, vasculitis, gout, adrenoleukodystrophy, diabetic retinopathy, nephropathy and diabetes mellitus type II.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: National Cholesterol Education Program, Second report of the Expert Panel on Detection, Evaluation, and Treatment of High Blood Cholesterol in Adults (Adult Treatment Panel II), National Institute of Health, National Heart Lung and Blood Institute, NIH Publication No. 93-3095, September 1993; abbreviated version: Expert Panel on Detection, Evaluation, and Treatment of High Blood Cholesterol in Adults, Summary of the second report of the national cholesterol education program (NCEP) Expert Panel on Detection, Evaluation, and Treatment of High Blood Cholesterol in Adults (Adult Treatment Panel II), JAMA, 1993, 269, pp. 3015–23. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The oral dosage amount of the dihydroxy open acid statin, particularly a salt of a dihydroxy open acid statin such as simvastatin, and more particularly the ammonium salt or a crystalline form of the calcium salt of dihydroxy open acid simvastatin such as compound I, is from about 1 to 200 mg/day, and more preferably from about 5 to 160 mg/day. However, dosage amounts will vary depending on factors as noted above, including the potency of the particular compound. Although the active drug of the present invention may be administered in divided doses, for example from one to four times daily, a single daily dose of the active drug is preferred. As examples, the daily dosage amount may be selected from, but not limited to, 5 mg, 10 mg, 15 mg, 20 mg, 25 mg, 40 mg, 50 mg, 75 mg, 80 mg, 100 mg, 150 mg and 160 mg.

The active drug employed in the instant therapy can be administered in such oral forms as tablets, capsules, pills, powders, granules, elixirs, tinctures, suspensions, syrups, and emulsions. Oral formulations are preferred.

For the crystalline hydrated forms of the calcium salt of dihydroxy open acid simvastatin, for example compound I, administration of the active drug can be via any pharmaceutically acceptable route and in any pharmaceutically acceptable dosage form. This includes the use of oral conventional rapid-release, time controlled-release and delayed-release (such as described above) pharmaceutical dosage forms. An oral delayed-release dosage formulation of the instant drug is preferred, and particularly an enteric overcoat surrounding a rapid-release dosage unit, or the GEM controlled-release drug delivery device with an enteric overcoat surrounding the dosage unit, and most particularly an enteric overcoat surrounding a rapid-release dosage unit. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, particularly BHA, propyl gallate and combinations thereof, can also be added to stabilize the dosage forms; the use of at least one stabilizing agent is preferred with the instant composition. Preferably an antioxidant is employed with dihydroxy open acid simvastatin or a salt thereof, and particularly compound I. Other suitable components include gelatin, sweeteners, natural and synthetic gums such as acacia, tragacanth or alginates, carboxymethylcellulose, polyethylene glycol, waxes and the like.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels.

The instant invention also encompasses a process for preparing a pharmaceutical composition comprising combining a dihydroxy open acid statin with a pharmaceutically acceptable carrier. Also encompassed is the pharmaceutical composition which is made by combining a dihydroxy open acid statin with a pharmaceutically acceptable carrier.

In a broad embodiment, any suitable additional active agent or agents may be used in combination with the dihydroxy open acid statin in a single dosage formulation, or may be administered to the patient in a separate dosage formulation, which allows for concurrent or sequential administration of the active agents. One or more additional active agents may be administered with a dihydroxy open acid statin. The additional active agent or agents can be lipid lowering compounds or agents having other pharmaceutical activities, or agents that have both lipid-lowering effects and other pharmaceutical activities. Examples of additional active agents which may be employed include but are not limited to HMG-CoA synthase inhibitors; squalene epoxidase inhibitors; squalene synthetase inhibitors (also known as squalene synthase inhibitors); acyl-coenzyme A: cholesterol acyltransferase (ACAT) inhibitors, for example the compound known as F-1394 (described in J. Kusunoki et al., Jpn. J. Pharmacol. 67, 195–203 (1995) and in U.S. Pat. No. 5,120,738), and including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors such as SCH-58235, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib. Additionally, the dihydroxy open acid statins of this invention, for example compound I, may be used in combination with anti-retroviral therapy in AIDS infected patients to treat lipid abnormalities associated with such treatment, for example but not limited to their use in combination with HIV protease inhibitors such as indinavir, nelfinavir, ritonavir and saquinavir.

A therapeutically or prophylactically effective amount, as appropriate, of a crystalline hydrated form of the calcium salt of dihydroxy open acid simvastatin, for example compound I, can be used for the preparation of a medicament useful for inhibiting HMG-CoA reductase, as well as for treating and/or reducing the risk for diseases and conditions affected by inhibition of HMG-CoA reductase, such as treating lipid disorders, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 1 mg to 200 mg of a crystalline hydrated form of the calcium salt of dihydroxy open acid simvastatin, or more particularly about 5 mg to 160 mg.

A therapeutically or prophylactically effective amount, as appropriate, of a dihydroxy open acid statin can be used for the preparation of an oral medicament adapted for delayed-release, wherein substantial release of the statin after oral administration does not occur until after passage of the medicament through the stomach, or alternately wherein at least 90% of the statin is delivered in its dihydroxy open acid form to the intestinal mucosa of a patient after oral administration. Said oral medicaments are also useful for inhibiting HMG-CoA reductase, as well as for treating and/or reducing the risk for diseases and conditions affected by inhibition of HMG-CoA reductase, as described above.

The medicament comprised of a dihydroxy open acid statin, for example compound I, may also be prepared with one or more additional active agents, such as those described supra.

Simvastatin is a semi-synthetic product which can be made from the natural product lovastatin. Processes for preparing lovastatin and simvastatin are well documented in the published literature. For example, U.S. Pat. No. 4,231,938, herein incorporated by reference, describes a fermentation and isolation process for obtaining lovastatin using the microorganism Aspergillus terreus. U.S. Pat. Nos. 4,444,784, 4,820,850, 4,916,239 and 4,582,915, herein all incorporated by reference, describe methods for making dihydroxy open-acid and lactonized forms of simvastatin.

Compound I of the instant invention can generally be prepared as follows. Simvastatin and its dihydroxy open acid counterpart, including compound I, tend to form oxidative by-products; therefore, to minimize the formation of such by-products, it is preferred that the procedures used to make compound I are performed under an inert atmosphere such as nitrogen. Although compound I can be obtained without using an inert atmosphere, the purity of the desired product will not be optimized.

Hydrolysis of the lactone ring of simvastatin can be accomplished by treating simvastatin with at least one equivalent, and preferably a slight excess of one equivalent, of an aqueous base. If more than a slight excess of base is used, the excess base is preferably neutralized before proceeding to the salt formation step in order to prevent formation of insoluble calcium hydroxide or calcium carbonate by-product. The base employed for the hydrolysis can be an aqueous solution of a metal hydroxide or metal carbonate, for example but not limited to sodium hydroxide, potassium hydroxide, lithium hydroxide, sodium carbonate and potassium carbonate. Sodium hydroxide is preferred. The hydrolysis can be performed in water, an aqueous-protic organic solvent mixture, or an aqueous-aprotic organic solvent mixture. Suitable protic organic solvents include but are not limited to methanol (MeOH), ethanol (EtOH), isopropyl alcohol, n-propyl alcohol (propanol). Examples of suitable aprotic organic solvents include but are not limited to acetonitrile, dimethyl sulfoxide (DMF), N,N-dimethylformamide (DMSO), tetrahydrofuran (THF), tert-butyl methyl ether (MTBE) and toluene. Particularly, an aqueous ethanol or n-propyl alcohol solvent mixture may be used, and more particularly an aqueous n-propyl alcohol solvent mixture.

After the hydrolysis reaction is complete, the pH of the reaction mixture is adjusted to about 6 to 11, particularly 6 to 9, and more particularly 7 to 8.5, by addition of an acid. In this pH range, the dihydroxy open acid simvastatin will exist as a metal salt, for example as the sodium salt if the base used in the hydrolysis step is sodium hydroxide or sodium carbonate. Any acid that is capable of forming a soluble calcium salt such as calcium chloride or calcium citrate, is suitable. A soluble calcium salt is intended to be a salt that is soluble in the solvent sytem employed in the instant process. Preferably an acid such as acetic acid (HOAc) or a mineral acid is employed, particularly HCl.

The resulting pH-adjusted reaction mixture containing the metal salt of dihydroxy open acid simvastatin is next combined with a solution of about 0.50 to 0.55 equivalents of calcium acetate hydrate [$Ca(OAc)_2 \cdot xH_2O$] in water or an aqueous-organic solvent mixture, such as aqueous EtOH, MeOH, i-PrOH, n-PrOH, acetonitrile, DMF, DMSO, THF, and particularly aqueous EtOH or aqueous n-propyl alcohol. The pH-adjusted reaction mixture can be added to the calcium acetate hydrate solution, or the calcium acetate hydrate solution can be added to the pH-adjusted reaction mixture. The addition can occur all at once, or optionally it can be performed in portions overtime with periods of aging. For example, a small portion, e.g., about one-quarter, of the calcium acetate hydrate solution can be added to the pH-adjusted reaction mixture over a short period of time, for example over about 30 minutes, and then the resulting mixture can be allowed to age for an additional short period of time at room temperature, optionally followed by a further period of aging at a temperature up to about 50° C., for example from about 10° C. up to about 50° C., particularly from room temperature up to about 50° C., more particularly from about 30 to 40° C., and most particularly from about 30 to 35° C., after which the remaining calcium acetate hydrate solution can be added in portions over several hours at a temperature up to about 50° C., for example from about 10° C. up to about 50° C., particularly from room temperature up to about 50° C., and more particularly from about 30 to 40° C., and most particularly from about 30 to 35° C. Optionally, the reaction mixture can be seeded with crystalline Compound I.

Whether the pH-adjusted reaction mixture and the calcium acetate hydrate solution are combined at once or in portions, the resulting slurry must be aged until turnover of the resulting amorphous calcium salt of dihydroxy open acid simvastatin to the crystalline product is complete, usually for at least several hours. Complete turnover to the crystalline product can be assessed by standard techniques in the art, for example, by examining a sample of the product under a microscope. This aging step can be performed at a temperature up to about 50° C., for example from about 10° C. up to about 50° C., particularly from room temperature up to about 50° C., and more particularly from about 30 to 40° C., and most particularly from about 30 to 35° C. During the aging period or periods, the use of lower temperatures will lead to crystallized product; however, it has been found that as the temperature drops, the rate of crystal turnover becomes slower, making the procedure less time-efficient.

If necessary, the slurry is then allowed to cool to room temperature and is collected by suction filtration. The recovered solid is suction dried under a moist atmosphere (about 30 to 70% relative humidity, particularly 40 to 70%), preferably a moist inert atmosphere such as nitrogen, and particularly at a temperature from about 10 to 40° C., and more particularly 25 to 35° C. The final step of suction filtration in the recovery of compound I should be done under a moist atmosphere, and preferably a moist inert atmosphere in order to minimize oxidative by-products. If an additional step of adding an antioxidant to compound I is performed, as described below, then the final suction filtration is the one performed after combining the antioxidant with compound I.

As noted above, compound I has a tendency to oxidize upon contact with air, and one way to minimize oxidation is to perform the reaction sequence under an inert atmosphere. Additionally, one or more anti-oxidants such as BHA, BHT, propyl gallate, ascorbic acid, calcium metabisulphite, hydroquinone, nordihydroguaiaracetic acid (NDGA) or 7-hydroxycoumarin can be combined with compound I. This is done by agitating a slurry of compound I with one or more of the antioxidants and recovering the resulting solid by suction filtration.

Alternatively, the ammonium salt of dihydroxy open acid simvastatin can be used as the starting material to be combined with the calcium acetate hydrate, thus avoiding the hydrolysis and pH adjustment steps needed when starting with lactonized simvastatin. The other reaction conditions described above, such as solvents, temperatures, etc., can otherwise be employed.

Abbreviations which may appear herein are as follows: MeOH is methanol; EtOH is ethanol; PROH is propanol; HOAc is acetic acid; MeCN is acetonitrile; DMF is dimethyl sulfoxide; DMSO is N,N-dimethylformamide; $Ca(OAc)_2$ is calcium acetate; HPLC is high performance liquid chromatography; min. is minutes; h is hour(s); D.I. is de-ionized; NMR is nuclear magnetic resonance; EI MS is electron impact mass spectrum; HR-El MS is high resolution electron impact mass spectrum; RH is relative humidity. The "seed" used in the examples is Compound I.

EXAMPLE 1

Preparation of Crystalline Hydrated Calcium Salt of Dihydroxy Open Acid Simvastatin (Compound I)

A 22 L four-necked round bottom flask was equipped with a temperature probe, a $N_2$ inlet, an addition funnel, and an overhead stirrer. 8.0 L of 15% EtOH-$H_2O$ was added and the solution was purged with $N_2$ for 10 min. Simvastatin (396 g, 0.946 mol) was added, and the slurry was purged with $N_2$ for 5 min. Then 5N NaOH (198 mL) was added at room temperature. After about 1 hour, the hydrolysis reaction was complete as analyzed by HPLC (>99.9% conversion). The pH of the reaction solution was adjusted to 7 to 8.5 by addition of 1 N HCl (approx. 65 mL). A solution of Ca$(OAc)_2 \cdot H_2O$ (116.6 g, 0.662 mol) in 4.0 L of 60% EtOH-$H_2O$ was purged with nitrogen for 5 min. A 1.0 L portion of this solution was added to solution of the sodium salt over 30 min. The resulting slurry was aged at room temperature for 30 min, and then at 30 to 35° C. for 1–2 h.

The rest of $Ca(OAc)_2$ in EtOH-water was added over approx. 30 min at 30 to 35° C. The slurry was aged at 30 to 35° C. for 5 hours under atmosphere of $N_2$. The slurry was cooled to room temperature and was collected by suction-filtration. The wet cake was washed with 4 L 30% EtOH-H2O, 4 L 20% EtOH-$H_2O$, followed by 6 L×3 of D.I. water. The solid was suction dried under an atmosphere of moist $N_2$ (40 to 70% relative humidity) at room temperature for 4 days. Crystalline hydrated calcium salt of dihydroxy open acid simvastatin was obtained as a white powder.

The calcium salt was delumped with a single pass through a cleaned QUADRO™ COMIL® (Model 197S).

HPLC CONDITIONS

| | |
|---|---|
| Column: | YMC Basic 4.6 mm × 25 cm |
| Detector: | ABS 757 1 AU/volt output |
| Sample solvent: | EtOH/$CH_3CN$/$H_2O$ (1:1:1) |
| Column temp: | 25° C. (Anal. Dept. runs samples at 5° C. to prevent formation of simvastatin on column). |
| Flowrate: | 1.5 mL/min. |
| Wavelength: | 238 and 210 nm |

| Gradient: | Time (min.) | % $CH_3CN$ | % $H_2O$ (10 mM $_2HPO_4$— $KH_2PO_4$, pH = 6.5) |
|---|---|---|---|
| | 0.00 | 30 | 70 |
| | 20.00 | 45 | 55 |
| | 34.00 | 70 | 30 |
| | 39.00 | 70 | 30 |
| | 39.50 | 30 | 70 |
| | 43.00 | 30 | 70 |

Retention time of simvastatin open acid: 17.07 min.
Retention time of simvastatin: 32.90 min.

Spectral Data
$^1$H NMR (400 MHz, $CD_3OD$), δ 5.97 (d, J=9.6 Hz, 1H), 5.77 (dd, J=9.6, 5.2 Hz, 1H), 5.49 (m, 1H), 5.33 (m, 1H), 4.17 (m, 1H), 3.70 (m, 1H), 2.44–2.35 (m, 2H), 2.42 (dd, J=15.7, 3.6 Hz, 1H), 2.31–2.27 (m, 1H), 2.29 (dd, J=15.7, 8.4 Hz, 1H), 2.00 (ddd, J=15.7, 7.6, 2.4 Hz, 1H), 1.93 (m, 1H), 1.68 (m, 1H), 1.61–1.55 (m, 2H), 1.55 (m, 2H), 1.42 (m, 1H), 1.32 (m, 1H), 1.19 (m, 1H), 1.12 (s, 6H), 1.08 (d, J=7.2 Hz, 3H), 0.89 (d, J=7.2 Hz, 3H), 0.84 (t, J=7.6 hz, 3H) ppm.

$^{13}$C NMR (100.55 MHz, CD3OD), δ 182.3, 179.3, 134.1, 133.2, 130.3, 129.6, 72.5, 69.8, 45.1, 44.4, 44.1, 38.8, 38.3, 36.4, 34.3, 33.9, 32.0, 28.6, 25.9, 25.37, 25.36, 23.7, 14.3, 9.9 ppm EI MS: m/e: 437 (M+H), 419(M+H–H$_2$O), 303.

HR-EI MS: Calcd. for $C_{25}H_{38}O_5$ 418.2719; Found: 418.2712.

EXAMPLE 2

Preparation of Crystalline Hydrated Calcium Salt of Dihydroxy Open Acid Simvastatin (Compound I) with BHA A 22 L three-necked round bottom flask was equipped with a temperature probe, a N$_2$ inlet, an additional funnel, and an overhead stirrer. 8.0 L of 15% EtOH-H$_2$O was added and purged with N$_2$ for 10 min. Simvastatin (396 g, 0.946 mol) was added, and the slurry purged with N$_2$ for 5 min. 198 mL of 5N NaOH (0.993 mol, 1.05 equiv.) was then added at room temperature. The hydrolysis reaction is usually complete in 1 h. as analyzed by HPLC (>99.9% conversion). The pH of the reaction solution was adjusted to 7 to 8.5 by addition of 1 N HCl (about 65 mL).

A solution of Ca(OAc)$_2$-H20(91.7 g, 0.520 mol, 0.55 equiv.) in 4.0 L of 60% EtOH-H$_2$O was purged with nitrogen for 5 min. 1.0 L of this solution was added to reaction solution over 30 min. The slurry was aged at room temperature for 30 min, and then at 30 to 35° C. for 1–2 h. The rest of the Ca(OAc)$_2$ in EtOH-water was added in portions over 3h hours at 30–35° C. The slurry was allowed to age at 30 to 35° C. for 5 h under an atmosphere of N$_2$. The slurry was allowed to cool to room temperature and was collected by suction-filtration. The wet cake was washed with 4 L 30% EtOH-H$_2$O, 4 L 20% EtOH-H$_2$O, followed by 6 L×3 of D.I. water. The solid was suction dried under atmosphere of moist N$_2$ (40 to 70% RH) at room temperature to give 1.7 Kg of wet cake.

The above wet cake was placed in a clean 20 L three necked flask under atmosphere of nitrogen. A solution of BHA (2.603 g, 0.2 wt % equiv) in degassed 15% EtOH H$_2$O (8.5 L) was added, followed by addition of degassed water (2.55 L), and the slurry was agitated at room temperature for 1 to 2 h. The solid was collected by suction filtration under atmosphere of moist N) with no washing to give 1.49 Kg wet cake. The solid was suction dried under atmosphere of moist N$_2$ (40 to 70% RH) at room temperature for 4 days. The calcium salt title product was obtained as a white powder (94% yield. 99.4% A at 238 nm, 0.2wt % BHA, KF=7.3% wt).

EXAMPLE 3

Preparation of Crystalline Hydrated Calcium Salt of Dihydroxy Open Acid Simvastatin (Compound I) in Aqueous nPrOH: Conventional Addition Mode Step 1: Hydrolysis A 72 L three-necked round bottom flask was equipped with a temperature probe, a N$_2$ inlet, an additional funnel, and an overhead stirrer. 28.5 L of D.I. H$_2$O was added and purged with N$_2$ for 10 min. 1.5 Kg simvastatin was added, followed by 788mL of 5N NaOH in one portion at room temperature. The hydrolysis reaction is usually complete in 2 h. as analyzed by HPLC (>99.9% conversion). 1.5L of nPrOH was added and the pH of the reaction solution was adjusted to 9.5 to 11.0 by adding 2 N HOAc (about 170 mL).

Step, 2: Salt Formation 150 g of seed (Compound 1) was added to the above solution and the resulting slurry was allowed to warm up to 35 to 40° C. A solution of Ca(OAc)$_2$.H$_2$O (347 g) in 15 L of 20% nPrOH was purged with nitrogen for 5 min. and added to slurry over 3 h. The resulting slurry was aged at 35 to 40° C. for 5 h. under an atmosphere of N$_2$ and then cooled to room temperature. The solid was collected by filtration and was washed with 10% nPrOH-H$_2$O (15 L×3).

Step 3: BHA loading

The above wet cake (9.1 kg) was transferred into a clean 72 L three necked flask under an atmosphere of nitrogen. A solution of BHA (7.6 g) in degassed 10% nPrOH (45 L) was added and the slurry was agitated at room temperature for 1 h. and filtered under atmosphere of N$_2$, and then suction dried under atmosphere of moist N$_2$ (30 to 70% RH) at room temperature for 7 days. 1.78 Kg of Ca salt title product was obtained as a white powder (94% yield. 99.4% A at 238 nm, 0.2wt % BHA, KF=6.6% wt).

EXAMPLE 4

Preparation of Hydrated Crystalline Calcium Salt of Dihydroxy Open Acid Simvastatin in Aqueous PrOH: Simultaneous Addition Mode The process described in this example allows for keeping half of the batch in the vessel at all times as seed in a semi-continuous process.

100 g of simvastatin was hydrolyzed in 1.9 L water as described in Example 3. Then, 100 ml nPrOH was added and the solution pH was adjusted to 9 to 11 with 1 N HOAc. The resulting solution and a solution of Ca(OAc)$_2$.H$_2$O (23.2 g) in 1.0 L of 20% nPrOH were added separately but simultaneously to a suspension of 10–50 wt % Ca salt in 10% nPrOH (30 volume 10% PrOH relative to the amount of the seed) at 30 to 40° C. over 3 h. After 5 h age at 30 to 40° C., the slurry was cooled to room temperature, filtered, and loaded with anti-oxidant and dried as described in conventional addition mode process. 95% yield.

EXAMPLE 5

Preparation of Crystalline Hydrated Calcium Salt of Dihydroxy Open Acid Simvastatin (Compound I) in Aqueous PrOH: Loading BHA Through Co-crystallization Method A: 100 g of simvastatin was hydrolyzed in 1.9 L water as described in Example 3. Then, 100 ml nPrOH was added and the solution pH was adjusted to 9 to 11 with 1 N HOAc. 10 wt % seed was added and the slurry was allowed to warm up to 35 to 40° C. A solution of Ca(OAc)$_2$.H$_2$O (23.2 g) and BHA (540 mg) in 1.0 L of 20% nPrOH were added to the slurry at 35 to 40° C. over 3 h. After 5 h age at 30 to 40° C., the slurry was cooled to room temperature, filtered and washed with a solution of BHA (0.1 g/L) in 10% nPROH (1L×3). The wet cake was dried under moist N$_2$ as described in conventional addition mode process. The final dried Ca salt title product contained 0.2 wt % BHA. 95% yield.

Method B: The procedure of Method A was employed with the following change. Instead of adding BHA to a Ca(OAc)$_2$ solution, the same amount of BHA was added into the pH adjusted solution of hydrolyzed simvastatin at room temperature. The solution was warmed to 35 to 40° C. to dissolve BHA. Then, 10 wt % seed was introduced. The rest of the steps were as described in Method A. The final dried Ca salt title product contained 0.2 wt % BHA. 95% yield.

EXAMPLE 6

Preparation of Crystalline Hydrated Calcium Salt of Dihydroxy Open Acid Simvastatin (Compound I) in Aqueous PrOH: Loading BHA/propyl Gallate Starting with 2.0 Kg of simvastatin, the calcium salt of dihydroxy open acid simvastatin was crystallized, isolated, and washed as described in Example 3. The first wet cake was transferred to a clean 100 L vessel under atmosphere of $N_2$. A solution of BHA (9.2 g) and propyl gallate (11.2 g) in 50 L 10% nPrOH was added to above vessel. The slurry was aged at room temperature for 1 h. The slurry was filtered with no wash. The wet cake was dried under moist $N_2$. 95% yield. The dried salt was loaded with 0.07 wt % propyl gallate and 0.2 wt % BHA.

EXAMPLE 7

Preparation of Crystalline Hydrated Calcium Salt of Dihydroxy Open Acid Simvastatin (Compound I) in Aqueous PROH: Loading Propyl Gallate Starting with 2.0 Kg of simvastatin, the calcium salt of dihydroxy open acid simvastatin was crystallized, isolated, and washed as described in Example 3. Then, the wet cake was washed with 10 L of a solution of propyl gallate in 10% nPrOH (propyl gallate concentration=0.224 g/L). Then, 20 L of propyl gallate solution in 10% nPrOH (propyl gallate concentration=0.224 g/L) was added and the wet cake was mixed in the filtration pot before filtration. The wet cake was dried under moist $N_2$. 95% yield. The dried salt was loaded with 0.07 wt % propyl gallate.

EXAMPLE 8

Preparation of Crystalline Hydrated Calcium Salt of Dihydroxy Open Acid Simvastatin (Compound I) Loading BHA, BHA/Vitamin E, and Vitamin E in Heptane 100 g of sirhvastatin was hydrolyzed in 1.9 L water as described in Example 3. Then, 100 ml nPrOH was added and the solution pH was adjusted to 9 to 11 with 1 N HOAc. 10 wt % seed was added and the slurry was allowed to warm up to to 40° C. A solution of Ca(OAc)$_2$.H$_2$O (23.2 g) in 1.0 L of 20% nPrOH was added to a slurry at 35 to 40° C. over 3 h. After 5 h age at 30 to 40° C., the slurry was cooled to room temperature. The calcium salt slurry was filtered and washed with 10% nPrOH (500 mL×1), followed by water (1L×3). The wet cake (KF=75 to 80 wt % water) was then washed with 1 L of heptane, to displace most of the water. This wet cake was washed with a solution of BHA or Vitamin E or BHA/Vitamin E (conc.=1.38 g/L, 800 mL) and dried under moist $N_2$.

EXAMPLE 9

Preparation of Crystalline Hydrated Calcium Salt of Dihydroxy Open Acid Simvastatin (Compound I) in Aqueous MeCN A 7.2 L three-necked round bottom flask was equipped with a temperature probe, a $N_2$ inlet, an additional funnel, and an overhead stirrer. 2.1 L of D.I. H$_2$O was added and purged with $N_2$ for 10 min. 150 g simvastatin was added, followed by 78.8mL of 5N NaOH in one portion at room temperature. The hydrolysis reaction is usually complete in 2 h. as analyzed by HPLC (>99.9% conversion). 900 mL of MeCN was added and the pH of the reaction solution was adjusted to 9.5 to 11.0 by adding 2 N HOAc (about 17 mL).

30.0 g crystalline seed was added to above solution and the resulting slurry was allowed to warm up to 30 to 35° C. A solution of Ca(OAc)$_2$.H$_2$O (34.7 g) in 1.5 L of 30% MeCN was purged with nitrogen for 5 min. and added to reaction slurry over 3 h. The slurry was at 35 to 40° C. for 5 h. under atmosphere of $N_2$. The slurry was allowed to cool to room temperature and the solid was collected by filtration. The wet cake was washed with 30% MeCN (1.5 L) and 10% MeCN (1.0 L), and rinsed/washed with a solution of BHA (0.9 g/L) in degassed 10% MeCN (1.0 L×2). The solid was suction dried under atmosphere of moist $N_2$ (30 to 70% RH) at room temperature for 5 days. 1.67 Kg of the title compound was obtained as a white powder (88% yield. 99.4% A at 238 nm, 0.2 wt % BHA, KF=6.6% wt).

EXAMPLE 10

Preparation of Crystalline Hydrated Calcium Salt of Dihydroxy Open Acid Simvastatin (Compound 1) in Aqueous MeOH 50 g simvastatin was hydrolyzed in 850 mL water as described in Example 3. Then, 150 ml MeOH was added and the solution pH was adjusted to 7 to 11 with IN HOAc. 10 wt % seed was added and the slurry was allowed to warm up to 30–35° C. A solution of Ca(OAc)$_2$.H$_2$O (11.6 g) in 500 mL of 30% MeOH was added to the slurry at 30–35° C. over 3 h. After 5 h age at 30–35° C., the slurry was cooled to room temperature. The dihydroxy open acid simvastatin calcium salt slurry was filtered and washed with 20% MeOH (200 ml) and water (500 ml×3). The wet cake was dried under moist $N_2$. The final dried Ca salt title product was isolated in 96% yield.

EXAMPLE 11

Preparation of Crystalline Hydrated Calcium Salt of Dihydroxy Open Acid Simvastatin (Compound I) in Aqueous i-PrOH, DMF, DMSO 50 g simvastatin was hydrolyzed in 850 mL water as described in Example 3. Then, 150 ml i-PrOH was added and the solution pH was adjusted to 7 to 11 with 1 N HOAc. 10 wt % seed was added and the slurry was allowed to warm up to 30–35° C. A solution of Ca(OAc)$_2$.H$_2$O (11.6 g) in 500 mL of 30% i-PrOH was added to the slurry at 30–35° C. over 3 h. After 5 h age at 30–35° C., the slurry was cooled to room temperature. Ca salt slurry was filtered and washed with 20% ml i-PrOH (200 ml) and with water (500 ml×3). The wet cake was dried under moist $N_2$. The final dried Ca salt title product was isolated in 96% yield.

The same procedure could be applied to prepare Compound I in DMF, DMSO, and similar solvents.

EXAMPLE 12

Preparation of Crystalline Hydrated Calcium Salt of Dihydroxy Open Acid Simvastatin (Compound I) in Water 50 g of simvastatin was hydrolyzed in 1.0 L water as described in Example 3. Then, the solution pH was adjusted to 11 with 1 N HOAc. 10 wt % seed was added and the slurry was allowed to warm up to 35–40° C. A solution of Ca(OAc)$_2$.H$_2$O (11.6 g) in 500 mL of water was added to the slurry at 35–40° C. over 5 h. After 10 h age at 35–40° C., the slurry was cooled to room temperature. Ca salt slurry was filtered and washed with water (500 ml×3). The wet cake was dried under moist N$_2$. The final dried Ca salt title product was isolated in 96% yield.

EXAMPLE 13

Preparation of Crystalline Hydrated Calcium Salt of Dihydroxy Open Acid Simvastatin (Compound I) from Dihydroxy Open Acid Simvastatin Ammonium Salt Method A: 50 g of dihydroxy open acid simvastatin ammonium salt was dissolved into 800 ml of 25% nPrOH which was then added dropwise to a solution of Ca (OAc)$_2$.H$_2$O (10.7 g) in 75 ml of water at room temperature over 2 h. The resulting slurry was aged at 30 to 35° C. 5 h. After cooling to room temperature, the slurry was isolated by filtration. The wet cake was washed with 10% nPrOH (500 ml×3). The wet cake was loaded with antioxidants and dried under moist N$_2$ as described above to give the title product.

Method B: 50 g of dihydroxy open acid simvastatin ammonium salt was added into a solution of Ca(OAc)$_2$.H$_2$O (10.7 g) in 1.5 L of 10% nPrOH in one portion at room temperature. The resulting slurry was aged at 30 to 35° C. 5 h. After cooling to room temperature, the slurry was isolated by filtration. The wet cake was washed with 10% nPrOH (500 ml×3). The wet cake was loaded with antioxidants and dried under moist N$_2$ as described above to give the title product.

By using both Methods A and B described as above, the title product could also prepared from ammonium salt in the following aqueous solvents: acetone, MeOH, EtOH, iPrOH, MeCN, neat water, DM, DMSO, and similar solvents.

EXAMPLE 14

Recrystallization Procedure Using nPrOH—H$_2$O

Dried Compound I (21 g) was dissolved in 150 ml of 40% nPrOH at 35° C. and line filtered. This solution was added dropwise to a slurry of 10 wt % seed in 480 ml of 4% PROH at 35 to 40° C. over 3 to 5 h. After aging overnight at 35 to 40° C., the slurry was allowed to cool to room temperature. The solid was filtered and washed with 10% nPrOH (200 ml×2). The wet cake was dried under moist N$_2$. 95% yield.

EXAMPLE 15

Recrystallization Process Using EtOH—H$_2$O

Method A: 25 g of Compound I was dissolved into 425 ml of 95% EtOH at 40° C. and line filtered. The filtered solution was added dropwise to 825 ml of water in the presence of 10% wt seed at 30 to 35° C. over 3 to 5 h. The slurry was aged overnight and cooled to 0 to 5° C. before filtration. The wet cake was washed with 250 ml of 30% EtOH and dried under moist N$_2$ at room temperature. 92% yield.

Method B: 25 g of Compound I was dissolved into 625 ml of 95% EtOH at 30 to 40° C. and line filtered. 525 ml of water was added at 30 to 40° C. After adding 10 wt % seed, 825 ml of water was added dropwise at 30 to 40° C. over 3 h. The slurry was aged overnight and cooled to 0 to 5° C. before filtration. The wet cake was washed with 250 ml of 30% EtOH and dried under moist N$_2$ at room temperature. 92% yield.

EXAMPLE 16

An open, randomized, four-period, crossover study to compare the effect of traconazole on the single-dose pharmacokinetics of intraduodenally administered dihydroxy open acid simvastatin versus orally administered simvastatin in healthy male subjects Objectives: (1) To determine the effect of itraconazole, a potent CYP3A inhibitor, on the plasma AUC of active and of total IMG-CoA reductase inhibitory activity following a single intraduodenal dose of a solution containing 5 mg dihydroxy open acid simvastatin; (2) to determine and compare the dose-adjusted plasma AUC of active HMG-CoA reductase inhibitory activity following a single intraduodenal dose of a solution containing 5 mg dihydroxy open acid simvastatin versus a single oral administration of simvastatin 20-mg film coated tablet (FCT); (3) to determine the effect of itraconazole on the plasma AUC's of dihydroxy open acid simvastatin and of simvastatin lactone concentration following a single intraduodenal dose of a solution containing 5 mg dihydroxy open acid simvastatin.

Study Design: This study was designed in an open, four-period crossover randomized fashion. Twelve healthy male subjects received four treatments (A, B, C and D). In Treatment A, subjects received itraconazole 200 mg (2×100-mg capsule) for 4 days followed by a single dose of 5-mg dihydroxy open acid simvastatin solution administered intraduodenally on day 4, 1 hour after the fourth daily dose of itraconazole. In Treatment B, subjects were given a single dose of 5-mg dihydroxy open acid simvastatin solution administered intraduodenally on day 1. Intraduodenal administration was accomplished via a nasoduodenal tube placed under fluoroscopic guidance by an experienced gastroenterologist just prior to dosing and removed following the 1-hr postdose measurements. Treatments C and D were similar to those of Treatments A and B, except that orally dosed simvastatin 20-mg conventional film coated tablet was used. The wash out between treatment periods was at least 7-days following a treatment containing itraconazole or at least 3 days following a treatment without itraconazole. Plasma samples were collected at appropriate time intervals for up to 24 hours following simvastatin or dihydroxy open acid simvastatin administration, for analysis of total and active HMG-CoA reductase inhibitory activities as well as for simvastatin and dihydroxy open acid simvastatin concentrations.

Analytical Methodology: Plasma concentrations of simvastatin and dihydroxy open acid simvastatin acid were determined simultaneously by an improved liquid chromatography/tandem mass spectrometry (LC/MSIMS) method using lovastatin and dihydroxy open acid lovastatin acid as internal standards. An enzymatic assay method was used to determine plasma concentrations of active and total (active plus potentially active) HMG-CoA reductase inhibitory activity.

Pharmacokinetics: The area under the plasma concentration-time profile from time zero to the last sampling time (AUCO-last) was calculated using linear trapezoidal rule. The apparent elimination rate constant (k) of simvastatin and dihydroxy open acid simvastatin was estimated by least-squares regression analysis of the log-linear portion of the simvastatin and dihydroxy open acid simvastatin concentration-time data, and the apparent elimination half-life ($t_{1/2}$) was calculated as $t_{1/2}=0.693/k$. All calculations were based on designated sampling times or actual sampling times when they differed from the designated times by more than 10 minutes.

Discussion of Results: This was an open, randomized, four-period crossover study in twelve healthy male subjects. The results showed that intraduodenal administration of dihydroxy open acid simvastatin 5-mg solution yielded higher (~4-fold) dose-adjusted plasma AUC of the active HMG-CoA reductase inhibitory activity than oral administration of simvastatin 20-mg tablet (Table 1). Following dihydroxy open acid simvastatin administration, the unchanged dihydroxy open acid simvastatin was the major component (~60%), while simvastatin was a minor component (<10%) contributing to plasma HMG-CoA reductase inhibitory activity. As evident by comparable AUC values for both the total and active inhibitors (see Table 1) as well as low plasma levels of simvastatin in plasma (AUC <10% of dihydroxy open acid simvastatin AUC) (see Table 3), lactonization of either dihydroxy open acid simvastatin or its active metabolites occurred minimally following intraduodenal administration of dihydroxy open acid simvastatin. Pretreatment with itraconazole caused minimal changes (1.3–1.5-fold) in the systemic exposure as measured by AUC and $C_{max}$ of HMG-CoA reductase inhibitory activity (total or active) following administration of dihydroxy open acid simvastatin 5-mg intraduodenally, as compared to that observed following oral administration of simvastatin 20-mg tablet (1.3–3.8-fold) (see Table 2) When measured as the unchanged drug, the effect of itraconazole observed following dihydroxy open acid simvastatin administration was also minimal (1.5-fold) and was much less than the corresponding measure obtained following simvastatin administration (19-fold) (see Table 3). A moderate effect (3–4-fold increase) was noted for the AUC and Cmax of simvastatin following treatment with itraconazole prior to dihydroxy open acid simvastatin administration (see Table 3). However, apparent t½ values for dihydroxy open acid simvastatin or simvastatin were essentially unchanged by itraconazole(see Table 3). Overall, these results indicate that the pharmacokinetics of dihydroxy open acid simvastatin is less prone to alteration by itraconazole, a potent CYP3A inhibitor, than that of simvastatin in humans. From these results it appears that dihydroxy open acid simvastatin, although a substrate for CYP3A, is metabolized with a much lower intrinsic clearance than that of simvastatin in human liver microsomes.

TABLE 1

Pharmacokinetic parameters for total and active HMG-CoA reductase inhibitors following administration of 5-mg dihydroxy open acid simvastatin (SVA) intraduodenally or 20-mg simvastatin (SV) tablet orally to 12 healthy male volunteers. Results are means from 12 subjects. Values in parentheses are SD.

| Drug Administered | | 5 mg SVA (ID) | 20 mg SV (FCT) |
|---|---|---|---|
| N | | 12 | 12 |
| AUC (ng eq. hr/ml) | Total | 56.0 (28.6) | 180.7 (57.2) |
|  | Active | 54.1 (28.5) | 59.7 (18.1) |
|  | SV | 1.02 (0.5) | 16.9 (10.5) |
|  | SVA | 33.9 (16.7) | 7.7 (4.9) |
| Cmax (ng eq./ml) | Total | 6.2 (3.6) | 67.1 (27.2) |
|  | Active | 5.7 (3.0) | 16.1 (4.4) |
|  | SV | 0.13 (0.05) | 6.84 (4.6) |
|  | SVA | 3.78 (1.93) | 0.92 (0.58) |
| Tmax (hr) | Total | 3.3 (2.3) | 1.2 (0.5) |
|  | Active | 3.6 (2.5) | 1.4 (0.5) |
|  | SV | 4.9 (2.0) | 1.1 (0.5) |
|  | SVA | 4.1 (2.1) | 3.7 (2.1) |
| t1/2 (hr) | SV | 6.7 (1.7) | 4.2 (1.9) |
|  |  | n = 8 |  |
|  | SVA | 2.3 (0.5) | 3.5 (1.0) |

TABLE 2

Pharmacokinetic parameters for total HMG-CoA reductase inhibitor following administration of 5-mg dihydroxy open acid simvastatin (SVA) intraduodenally or 20-mg simvastatin (SV) tablet orally with or without pretreatment with itraconazole (2 × 100-mg capsule, qd) for 4 days to 12 healthy male volunteers. Results are means from 12 subjects. Values in parentheses are SD.

| Treatment | AUC (ng eq·hr/mL) | Cmax (ng eq/mL) | Tmax (hr) |
|---|---|---|---|
| Total Inhibitors | | | |
| Single 5-mg SVA (ID) + 4 Days of Daily 200-mg Itraconazole | 86.1 ± 47 | 8.2 ± 4.0 | 4.3 ± 2.2 |
| Single 5-mg SVA (ID) | 56.0 ± 28.6 | 6.2 ± 3.6 | 3.3 ± 2.3 |
| Geometric Mean Ratio | 1.5 | 1.3 | |
| Single 20-mg SV (CT) + 4 Days of Daily 200-mg Itraconazole | 683 ± 232 | 126 ± 54.8 | 1.9 ± 0.9 |
| Single 20-mg SV (CT) | 180.7 ± 57.2 | 67.1 ± 27.2 | 1.2 ± 0.5 |
| Geometric Mean Ratio | 3.8 | 1.9 | |
| Active Inhibitors | | | |
| Single 5-mg SVA (ID) + 4 Days of Daily 200-mg Itraconazole | 75.0 ± 39.6 | 7.4 ± 3.9 | 5.5 ± 1.7 |
| Single 5-mg SVA (ID) | 54.1 ± 28.5 | 5.7 ± 3.0 | 3.6 ± 2.5 |
| Geometric Mean Ratio | 1.3 | 1.3 | |
| Single 20-mg SV (CT) + 4 Days of Daily 200-mg Itraconazole | 195 ± 104 | 23.0 ± 13.6 | 3.1 ± 0.9 |
| Single 20-mg SV (CT) | 59.7 ± 18.1 | 16.1 ± 4.4 | 1.4 ± 0.5 |
| Geometric Mean Ratio | 3.1 | 1.3 | |

TABLE 3

Pharmacokinetic parameters for simvastatin or dihydroxy open acid simvastatin following administration of 5-mg dihydroxy open acid simvastatin (SVA) intraduodenally or 20-mg simvastatin (SV) tablet orally with or without pretreatment with itraconazole (2 × 100-mg capsule, qd) for 4 days to 12 healthy male volunteers. Results are means from 12 subjects. Values in parentheses are SD.

| Treatment | AUC (ng eq·hr/mL) | Cmax (ng eq/mL) | t1/2 (hr) | Tmax (hr) |
|---|---|---|---|---|
| Simvastatin | | | | |
| Single 5-mg SVA (ID) + 4 Days of Daily 200-mg Itraconazole | 5.18 ± 3.15 | 0.43 ± 0.2 | 6.7 ± 2.5 (n = 11) | 5.3 ± 1.9 |
| Single 5-mg SVA (ID) | 1.02 ± 0.5 | 0.13 ± 0.05 | 6.7 ± 1.7 (n = 8) | 4.9 ± 2.0 |
| Geometric Mean Ratio | 4.4 | 3.2 | 1.0 | |
| Single 20-mg SV(CT) + 4 Days of Daily 200-mg Itraconazole | 316 ± 142 | 77.2 ± 50.7 | 5.2 ± 1.5 | 1.8 ± 1.1 |
| Single 20-mg SV (CT) | 16.9 ± 10.5 | 6.84 ± 4.6 | 4.2 ± 1.9 | 1.1 ± 0.5 |
| Geometric Mean Ratio | 19.4 | 11.4 | 1.3 | |
| Simvastatin Acid | | | | |
| Single 5-mg SVA (ID) + 4 Days of Daily 200-mg Itraconazole | 56.8 ± 33.5 | 5.78 ± 3.27 | 2.8 ± 1.1 | 4.7 ± 2.4 |
| Single 5-mg SVA (ID) | 33.9 ± 16.7 | 3.78 ± 1.93 | 2.3 ± 0.5 | 4.1 ± 2.1 |
| Geometric Mean Ratio | 1.5 | 1.5 | 1.1 | |
| Single 20-mg SVA (CT) + 4 Days of Daily 200-mg Itraconazole | 86.2 ± 65.6 | 9.76 ± 7.38 | 4.5 ± 1.3 | 4.0 ± 1.4 |
| Single 20-mg SV (CT) | 7.70 ± 4.9 | 0.92 ± 0.58 | 3.5 ± 1.0 | 3.7 ± 2.1 |
| Geometric Mean Ratio | 11.0 | 10.7 | 1.3 | |

EXAMPLE 17

Coating Formulation and Process: SURETERIC WHITE®

SURETERIC WHITE® is a powdered enteric coating formulation available from Colorcon, a division of Berwind Pharmaceutical Services, Inc, West Point, Pa. This formulation is first reconstituted with water, then coated as an aqueous dispersion. In addition to PVAP, the polymer which imparts the enteric properties, the formulation contains a number of components to improve the processability of the material and the performance of the final coated product. The dispersion is stirred during preparation and during the coating run, in order to prevent settling of the formulation components.

The tablet substrate was coated in a 19-inch coating pan, with a batch size of approximately 4–8 kg. The coating formulation was applied via a spray nozzle at a rate of approximately 20–40 g/min, and pressurized air was used to atomize the coating solution. During the coating operation heated air was introduced into the coater to maintain the tablet bed temperature at approximately 35–45 degrees C. Outside this temperature range, the tablet bed is more likely to agglomerate due to either inadequate drying (low temperature) or to the tackiness of the enteric polymer, which increases at elevated temperatures.

During the coating operation, the weight and/or thickness gain of the dosage form can be used to monitor the coating endpoint. A weight gain of approximately 10% (based on the starting weight of the dosage form) was targeted for this product, corresponding to an approximate coating thickness of 100 microns.

EXAMPLE 18

Coating Formulation and Process: EUDRAGIT®

EUDRAGIT L® aqueous dispersion with additional water, a plasticizer, and an antitacking agent are combined to obtain the final formulation. The formulation is mixed constantly during preparation and during the coating operation, in order to prevent sedimentation of the formulation components.

A batch of approximately 1 kg of tablets was placed into a 12-inch coating pan; and heated air was introduced to the coater to maintain a temperature of approximately 25–35 degrees C for the duration of the coating operation. The coating formulation was applied via a spray nozzle at a rate of approximately 3–6 g/min, and pressurized air was used to atomize the coating solution. The coating temperature and spray rate are controlled in order to prevent agglomeration of the product due to overwetting or polymer tackiness.

During the coating operation, the weight and/or thickness gain of the dosage form can be used to monitor the coating endpoint. A weight gain of approximately 4–6 mg enteric polymer per $cm^2$ tablet surface area (approximately 40–80 micron coating thickness, and approximately 6–10% weight gain based on the starting weight of the dosage form) was targeted as the coating endpoint. (However, a range of coating levels outside this target has been shown to provide adequate product performance as well).

EXAMPLE 19

Core tablets comprised of compound I with a 50% hydroxypropyl cellulose/50% hydroxypropyl methyl cellulose with titanium dioxide sub-coat and SURETRIC WHITE® enteric coat ("Enteric Coated Tablets"), core tablets comprised of compound I without sub-coat or enteric coat ("Core Tablets"), and core tablets comprised of compound I with a sub-coat but no enteric coat ("Sub-Coated Tablets") were tested at the temperature, humidity levels and time points noted in Table 4 below. The amount of API (active pharmaceutical ingredient, which is compound I) in the tablet was measured at the beginning of the study. At the specified timepoint, the API was remeasured and reported as a percentage of the value measured at the beginning of the study (%initial). The amount of deg(s) (degradent(s))was also measured at the end of the indicated study period and expressed as % label claim based on the total theoretical drug content (label claim) of the tablet. The label claim for all tested tablets was 25 mg of compound I per tablet. RH is relative humidity; AMB is ambient; and "Lactone" refers to simvastatin.

In all cases, core tablets and sub-coated tablets did not exhibit enhanced stability as indicated by a decrease in API content in the tablets. However, tablets coated with SURETERIC WHITE® showed remarkably improved stability at all temperature and humidity stations. These results are summarized below.

TABLE 4

| Station Timepoint | Enteric Coated Tablets | | | Core or Sub-Coated* Tablets | | |
|---|---|---|---|---|---|---|
| | API % Initial | Lactone (Deg.) % label claim | Total Other Degs. (>0.1%) % label claim | API % Initial | Lactone (Deg.) % label claim | Total Other Degs. (>0.1%) % label claim |
| 40° C./75% RH 4 weeks | 100 | 0.37 | 0 | 87.3* | 5.21* | 0.73* |
| 40° C./75% RH 4 weeks | 100.5 | 0.47 | 0 | 93.7 | 6.37 | 0.70 |
| 60° C./AMB RH 1 week | 97.0 | 0.39 | 0.10 | 69.3 | 0.21 | 4.6 |
| 60° C./AMB RH 1 week | 100.6 | 0.17 | 0.21 | 34.8 | 0.12 | 7.6 |
| 60° C./AMB RH 1 week | 99.4 | 0.31 | 0 | 62.8 | 0.22 | 4.7 |
| 60° C./AMB RH 1 week | 98.7 | 0.24 | 0.13 | 72.6 | 0.20 | 3.16 |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. An oral pharmaceutical composition comprising a therapeutically effective amount of a statin selected from the group consisting of the dihydroxy open acid forms of lovastatin, simvastatin, pravastatin and atorvastatin and the pharmaceutically acceptable salts and esters thereof and a pharmaceutically acceptable carrier, formulated in an enteric coated dosage form wherein substantial release of the compound from the dosage form after oral administration to a patient is delayed until after passage of the dosage form through the stomach.

2. The pharmaceutical composition of claim 1 wherein the dosage form is surrounded by an enteric coating.

3. The pharmaceutical composition of claim 1 wherein the dosage form comprises enterically coated granules of the statin.

4. The pharmaceutical composition of claim 3 wherein the dosage form comprises enterically coated granules of dihydroxy open acid simvastatin or a pharmaceutically, acceptable salt or ester thereof.

5. The pharmaceutical composition of claim 1 wherein the dosage form comprises enterically coated granules of the statin, provided that the dosage form does not contain granules of aspirin.

6. The pharmaceutical composition of claim 1 wherein the composition is formulated in an enterically coated rapid-release pharmaceutical dosage form.

7. The pharmaceutical composition of claim 1 wherein the composition is formulated in an enterically coated time controlled-release pharmaceutical dosage form.

8. The pharmaceutical composition of claim 1 wherein the composition is formulated in a drug delivery device comprised of:
   (A) a compressed core prepared from an admixture comprising:
      (i) a therapeutically effective amount of the statin; and
      (ii) a polymer which upon hydration forms gelatinous microscopic particles;
   (B) a water insoluble, water impermeable polymeric coating comprising a polymer and a plasticizer, which surrounds and adheres to the core, the coating having a plurality of formed apertures exposing between about 1 and about 75% of the core surface; and
   (C) an enteric overcoat exterior to the water insoluble, water impermeable polymeric coating;
   and wherein the release rate of the statin from the device is a function of the number and size of the apertures.

9. The composition of claim 1 wherein the statin is selected from the dihydroxy open acid form of lovastatin, simvastatin and the pharmaceutically acceptable salts and esters thereof.

10. The composition of claim 1 wherein the statin is selected from the dihydroxy open acid form of simvastatin and the pharmaceutically acceptable salts and esters thereof.

11. The composition of claim 1 wherein the statin is a pharmaceutically acceptable salt of dihydroxy open acid simvastatin.

12. The composition of claim 1 wherein the statin is a calcium salt of dihydroxy open acid simvastatin.

13. The composition of claim 1 wherein the statin is an ammonium salt of dihydroxy open acid simvastatin.

14. The composition of claim 1 wherein the statin is a crystalline hydrated calcium salt of dihydroxy open acid simvastatin having an x-ray powder diffraction pattern obtained using CuKα radiation characterized by reflections at d-spacings of 30.7, 24.6, 15.9, 11.2, 8.58, 7.31, 6.74, 6.06, 5.35, 5.09, 4.93, 4.60, 3.93, 3.84, 3.67, 3.51 and 3.28 Å.

15. The composition of claim 14 further comprising BHA.

16. The composition of claim 14 further comprising propyl gallate.

17. The composition of claim 14 further comprising BHA and propyl gallate.

18. The composition of claim 8 wherein the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

19. The composition of claim 18 wherein the enteric coating surrounds the dosage form.

20. The composition of claim 14 wherein the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

21. The composition of claim 20 wherein the enteric coating surrounds the dosage form.

22. The composition of claim 15 wherein the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

23. The composition of claim 16 wherein the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

24. The composition of claim 17 wherein the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

25. The composition of claim 17 wherein the dosage form is comprised of a core tablet, a sub-coat applied over the core tablet and an enteric coat applied over the sub-coat, wherein the core tablet is comprised of a crystalline hydrated calcium salt of dihydroxy open acid simvastatin having an x-ray powder diffraction pattern obtained using CuKα radiation characterized by reflections at d-spacings of 30.7, 24.6, 15.9, 11.2, 8.58, 7.31, 6.74, 6.06, 5.35, 5.09, 4.93, 4.60, 3.93, 3.84, 3.67, 3.51 and 3.28 Å, the sub-coat is comprised of a 1:1 ratio hydroxypropyl cellulose:hydroxypropyl methyl cellulose mixture, and the enteric coat is comprised of polyvinyl acetate phthalate, titanium dioxide, talc, colloidal silicon dioxide, triethyl citrate, polyethylene glycol, sodium bicarbonate, purified stearic acid and sodium alginate.

26. The composition of claim 25 wherein the core tablet is further comprised of an anti-oxidant agent selected from the group consisting of BHA, propyl gallate and combinations thereof.

* * * * *